(12) United States Patent
Rovatti et al.

(10) Patent No.: US 11,701,463 B2
(45) Date of Patent: Jul. 18, 2023

(54) INFUSION SET FOR MEASURING VITAL SIGNALS OF A PATIENT COMPRISING A COMPLIANCE ELEMENT AND A REFLECTIVE ELEMENT

(71) Applicants: Baxter International Inc., Deerfield, IL (US); Baxter Healthcare SA, Glattpark (CH)

(72) Inventors: Paolo Rovatti, Modena (IT); Mariano Ruffo, Naples (IT); David Stefani, Modena (IT); Elena Grandi, Modena (IT)

(73) Assignees: BAXTER INTERNATIONAL INC., Deerfield, IL (US); BAXTER HEALTHCARE SA, Clattpark (CH)

( * ) Notice: Subject to any disclaimer, the term of this patent is extended or adjusted under 35 U.S.C. 154(b) by 499 days.

(21) Appl. No.: 16/956,829

(22) PCT Filed: Dec. 21, 2018

(86) PCT No.: PCT/EP2018/086627
§ 371 (c)(1),
(2) Date: Jun. 22, 2020

(87) PCT Pub. No.: WO2019/122348
PCT Pub. Date: Jun. 27, 2019

(65) Prior Publication Data
US 2021/0001043 A1  Jan. 7, 2021

(30) Foreign Application Priority Data
Dec. 22, 2017 (EP) .................................. 17210526

(51) Int. Cl.
*A61M 5/172* (2006.01)
*A61M 5/142* (2006.01)
(Continued)

(52) U.S. Cl.
CPC .......... *A61M 5/142* (2013.01); *A61M 5/1411* (2013.01); *A61M 5/14228* (2013.01);
(Continued)

(58) Field of Classification Search
CPC ............ A61M 5/1411; A61M 5/16854; A61M 5/16813; A61M 5/142; A61M 5/1723
See application file for complete search history.

(56) References Cited

U.S. PATENT DOCUMENTS 4,345,594 A   8/1982   Bisera et al.
4,551,133 A   11/1985  Zegers de Beyl et al.
(Continued)

FOREIGN PATENT DOCUMENTS

CN   1839765 A    10/2006
CN   101032431 A  9/2007
(Continued)

OTHER PUBLICATIONS

European Office Action for related European Application No. 17210526.4; action dated Dec. 21, 2020; (7 pages).
(Continued)

*Primary Examiner* — Jenna Zhang
(74) *Attorney, Agent, or Firm* — K&L Gates LLP

(57) ABSTRACT

There is provided an IV infusion set comprising a patient access configured to connect to a vascular system of a patient, a source of medical fluid, an infusion line having one first end configured to connect to the source of medical fluid and one opposite second end configured to deliver the medical fluid towards the patient access, an infusion apparatus arranged on the infusion line, a sensor configured to emit a pressure signal indicative of a pressure of a medical fluid in the infusion line, and a control unit configured to receive the pressure signal and to determine a patient signal indicative of a vital signal of the patient based on the
(Continued)

pressure signal. The IV infusion set further comprises a compliance element configured to attenuate pressure variations of medical fluid the infusion line, and a resistance element configured to reflect pressure waves moving along the infusion line. The sensor is arranged on the infusion line at a position downstream from the resistance element with respect to a direction of fluid flow along the infusion line from the medical fluid source towards the patient access. The infusion line may include a main infusion line and/or one or more auxiliary infusion lines connected to a main infusion line.

25 Claims, 19 Drawing Sheets

(51) Int. Cl.
*A61M 5/14* (2006.01)
*A61M 5/168* (2006.01)

(52) U.S. Cl.
CPC .... *A61M 5/16813* (2013.01); *A61M 5/16854* (2013.01); *A61M 5/1723* (2013.01); *A61M 5/1407* (2013.01); *A61M 2205/3331* (2013.01); *A61M 2205/3341* (2013.01); *A61M 2206/22* (2013.01); *A61M 2230/06* (2013.01); *A61M 2230/30* (2013.01); *A61M 2230/42* (2013.01)

(56) References Cited

U.S. PATENT DOCUMENTS

| | | | |
|---|---|---|---|
| 4,979,940 | A | 12/1990 | Bobo, Jr. et al. |
| 7,927,270 | B2 | 4/2011 | Dlugos et al. |
| 8,016,744 | B2 | 9/2011 | Dlugos et al. |
| 9,474,846 | B2 | 10/2016 | Steger |
| 2006/0272421 | A1 | 12/2006 | Frinak et al. |
| 2007/0060874 | A1* | 3/2007 | Nesbitt .............. A61M 5/1408 604/80 |
| 2009/0026146 | A1 | 1/2009 | Carlisle et al. |
| 2011/0144531 | A1 | 6/2011 | Marcotte et al. |
| 2013/0331811 | A1 | 12/2013 | Butterfield |
| 2014/0276410 | A1* | 9/2014 | Rose .................. A61M 5/46 604/117 |
| 2015/0246173 | A1* | 9/2015 | Steger .............. A61M 1/3607 604/6.01 |

FOREIGN PATENT DOCUMENTS

| | | |
|---|---|---|
| CN | 101239010 A | 8/2008 |
| CN | 101607102 A | 12/2009 |
| CN | 202223648 U | 5/2012 |
| CN | 102512725 A | 6/2012 |
| CN | 103313740 A | 9/2013 |
| CN | 203829412 U | 9/2014 |
| CN | 104874036 A | 9/2015 |
| CN | 105636622 A | 6/2016 |
| EP | 3072495 A1 | 9/2016 |
| WO | 9804303 | 2/1998 |
| WO | 2007092618 A2 | 8/2007 |
| WO | 2011100134 A1 | 8/2011 |
| WO | 2012139593 A2 | 10/2012 |
| WO | 2015061723 A2 | 4/2015 |

OTHER PUBLICATIONS

European Search Report for related European Application No. 17210526; report dated Jun. 19, 2018; (4 pages).

International Search Report and Written Opinion for related International Application No. PCT/EP2018/086627; report dated Apr. 17, 2019; (16 pages).

Office Action issued in corresponding Chinese Patent Application No. 201880087387.5, received Dec. 6, 2021; (10 pages).

Office Action issued in corresponding Singapore Patent Application No. 11202005877W, dated Dec. 20, 2021; (7 pages).

* cited by examiner

INFUSION SET FOR MEASURING VITAL SIGNALS OF A PATIENT COMPRISING A COMPLIANCE ELEMENT AND A REFLECTIVE ELEMENT

CROSS-REFERENCE TO RELATED APPLICATIONS

The present application is a National Stage of International Application No. PCT/EP2018/086627, filed on Dec. 21, 2018, which claims the benefit of earlier filing date and right of priority to European Application No. 17210526.4 filed on Dec. 22, 2017, the contents of which are all hereby incorporated by reference herein in their entirety.

TECHNICAL FIELD

The present invention relates to an infusion set for measuring vital signals of a patient. In more detail, the invention refers to an infusion set for measuring vital signals of a patient comprising a compliance element and a reflective element.

The infusion set, for example including a main infusion line and an auxiliary infusion line, includes (on either one or on both of the lines) a compliance element, configured to absorb or attenuate pressure waves being transmitted through a medical fluid conveyed through the infusion set, and a resistance element, configured to amplify or intensify pressure waves. The compliance element and the resistance element are relatively positioned on an infusion line (e.g. main and/or auxiliary) with respect to a potential location for measuring the pressure of the medical fluid in the infusion line such that unwanted pump signal spectrum components or disturbances are absorbed or attenuated and such that a signal to be measured is amplified or intensified and unwanted components are attenuated or reduced. Unwanted pump signal spectrum components can result, for example, from the pump signal amplitude spectrum form, which may overlay or superpose a signal to be measured is amplified or intensified

BACKGROUND OF THE INVENTION

In medical applications it is often desired or required to measure vital signals of a patient to be treated before, during, and/or after treatment. Treatment may include infusion of a medical fluid to a cardiovascular system of a patient or extracorporeal treatment of a medical fluid, for example blood removed from a patient and/or returned to a patient.

Vital signs of a patient, for example the cardiac signal or the peripheral venous pressure, can be measured using an intravenous (IV) infusion set and by placing one or more sensors at one or more components of the IV infusion set. For example, the peripheral venous pressure (PVP) can be measured by measuring the line pressure (LP) within the IV infusion set, the LP being measured on the IV infusion line between the IV infusion pump and the venous access. During operation, however, pump pressure propagates along the IV infusion line from the pump to the venous access. The PVP propagates along the IV infusion line from the venous access towards the pump.

Measuring the LP may entail several problems. For example, during operation, the pump may generate an amplitude spectrum form, typically depending upon an operating speed of the pump. The pump signal amplitude spectrum propagates along the IV infusion line and can negatively impact an extraction and/or measurement of the LP. The particular placement of the sensor measuring/extracting the LP may have a substantial impact on the quality of the measurements and/or of the signal generated by the sensor.

It is desired to improve the signal/noise ratio for the measurements of the LP in order to be able to more accurately measure the PVP or other vital signs of a patient in view of unwanted spectrum components.

In order to address the above issues, it is known that the site at which the LP is measured may be moved towards the venous access in order to reduce the effects of the pump signal amplitude spectrum form and/or in order to be able to measure the PVP more accurately. However, due to particular effects (e.g. echo waves, resonance, etc.) the placement of the sensor is typically very difficult and may have to be adapted to a number of factors affecting the measurements, including, but not limited to, the type of infusion set used, an operating speed of the pump, a type of the infusion apparatus and/or pump used, liquid viscosity and or density, pump height regarding to the patient, and other factors.

Further, an absorbing element (e.g. a volume partially filled by gas; e.g. a drip chamber) may be inserted or moved to a position downstream from the pump (e.g. with respect to fluid flow, between a position of the pump and a position where the LP is measured). This may absorb pressure waves and/or the amplitude spectrum generated by the pump.

Problems occurring with prior art designs include that the dampening affects both the pump signal amplitude spectrum and the cardiac signal. It is further known that it might be difficult to shift the cut-off frequency of the dampener/absorber by simply changing a compliance thereof (e.g. through different flexibility of the chamber or through different inner volume of gas), since it is quite common that the pump signal amplitude spectrum has substantially the same frequency spectrum of the cardiac signal to be measured (typically between 0.5 to 3 Hz) and, thus, may substantially affect the measurements.

U.S. Pat. No. 4,551,133 A describes a medication infusion system including an infusion line, a pump, and a pressure transducer. Also included are electrical filters and amplifiers for processing the pressure signal. The infusion system may be used to monitor the respiration and heart rate from a peripheral vein. The system involves extensive signal processing based on electrical filters and amplifiers in order to derive, from the pressure signal, the respiratory rate and/or the heart rate of a patient. The system is designed to only activate the pump intermittently so that operation of the pump does not interfere with the pressure measurements.

U.S. Pat. No. 4,979,940 A describes monitoring fluid pressure in a conduit in order to detect pressure artifacts related to patient activity. The system includes an infusion pump, a pressure transducer, and an amplifier. A key focus of the system includes avoiding false alarms while detecting unwanted infiltration of fluid into tissue due to an incorrect placement of an IV infusion needle or due to the needle shifting its position during treatment.

WO 2015/061723 A2 describes a medical fluid injection manifold, including a manifold housing a dampening device for dampening pressure signals communicated from a patient to a pressure sensor. The manifold allows for a pressure sensor to be put into fluid communication with different fluid lines.

U.S. 2009/026146 A1 describes a flow control system for an infusion pump. The system allows the setting of a minimum pressure threshold, such that it is sensitive enough to avoid noise in a flow signal, for example induced by patient movement, while remaining sensitive to patient pressure. The system also provides means to detect an occlusion.

U.S. 2013/331811 A1 describes a drip chamber for dampening the pressure waves of the infusion pump, in which the drip chamber is located upstream of the pump. A main objective appears to be the dampening of pressure pulses propagating upstream from the intake of the pump. The system is based on a closed loop control, in which pressure and resistance can be continuously adjusted. Further, the damping effect is partly based on the drip chamber.

WO 98/04303 A1 describes monitoring the flow resistance of an infusion line by measuring pressure, for example in order to detect an occlusion of the administration line. The disclosure focuses on coping with noise sources, such as patient movement, breathing, etc. Further, effects of the use of several IV infusion sets in parallel are described.

U.S. 2006/272421 A1 describes detecting intravascular pressure, wherein a membrane can dampen the oscillations relating to cardiovascular system of a patient. The described concepts are also applicable to intravenous infusion.

SUMMARY

A general aim of the present invention is to provide an IV infusion set that alleviates or minimizes the above-mentioned drawbacks. It is a further aim of the present invention to provide an infusion line that alleviates or minimizes the above-mentioned drawbacks. It is yet a further aim of the present invention to provide a process for detecting the pressure of a medical fluid in an IV infusion set that alleviates or minimizes the above-mentioned drawbacks.

An IV infusion set, an infusion line, and/or a process according to one or more of the appended claims, taken singly or in any combination, attain at least one of the above-indicated aims.

In a $1^{st}$ independent aspect there is provided an IV infusion set, comprising a patient access configured to connect to a vascular system (86) of a patient, a source (40, 40a) of medical fluid, an infusion line having at least one first end configured to connect to the source of medical fluid and at least one opposite second end configured to deliver the medical fluid towards the patient access, the infusion line defining at least a medical fluid path developing from the first end of the infusion line to the patient access, the second end of the infusion line being connected to the patient access, the source of medical fluid being coupled to the first end of the infusion line and configured to supply medical fluid to the infusion line, an infusion apparatus arranged on the infusion line, a sensor configured to emit a pressure signal indicative of a pressure of a medical fluid in the infusion line, and a control unit configured to receive the pressure signal and to determine a patient signal indicative of a vital signal of the patient based on the pressure signal. The infusion apparatus includes a pump. The IV infusion set further comprises a compliance element configured to attenuate pressure variations of medical fluid the infusion line, and a resistance element configured to reflect pressure waves moving along the infusion line. The sensor is arranged on the infusion line at a position downstream from the resistance element with respect to a direction of fluid flow along the infusion line from the medical fluid source towards the patient access. Optionally, the infusion line includes a main infusion line with or without one or more auxiliary infusion lines connected to a main infusion line.

In accordance with any one of the aspects of the invention, the infusion line includes a main infusion line and at least one auxiliary infusion line connected to the main infusion line. The at least one auxiliary infusion line has at least one first end configured to connect to an auxiliary source of medical fluid and at least one opposite second end configured to deliver the medical fluid towards the main infusion line. The auxiliary infusion line defines at least a medical fluid path developing from the first end of the auxiliary infusion line to the patient access. The source of medical fluid is coupled to the first end of the auxiliary infusion line and configured to supply medical fluid to the auxiliary infusion line. The IV infusion set further comprises the auxiliary source of medical fluid, and an auxiliary infusion apparatus arranged on the auxiliary infusion line.

In accordance with any one of the aspects of the invention, in particular in accordance with the preceding aspect, the IV infusion set further comprises at least one auxiliary sensor configured to emit an auxiliary pressure signal indicative of a pressure of a medical fluid in the at least one auxiliary infusion line.

In accordance with any one of the two preceding aspects, the IV infusion set further comprises, for each of the at least one auxiliary infusion lines, an auxiliary compliance element configured to attenuate pressure variations of medical fluid in the respective auxiliary infusion line, and an auxiliary resistance element configured to reflect pressure waves moving along the respective auxiliary infusion line. The compliance element and the resistance element are arranged on the main infusion line and the auxiliary compliance element and the auxiliary resistance element are arranged on the auxiliary infusion line. Optionally, the auxiliary compliance element and the auxiliary resistance element are arranged on the auxiliary infusion line proximate the connection to the main infusion line.

In a $2^{nd}$ aspect according to any one of the preceding aspects, in particular according to aspect 1, the compliance element is arranged downstream from the pump with respect to the direction of fluid flow along the infusion line from the medical fluid source towards the patient access.

In a $3^{rd}$ aspect according to any one of the preceding aspects, the compliance element is arranged upstream from the resistance element with respect to the direction of fluid flow along the infusion line from the medical fluid source towards the patient access.

In a $4^{th}$ aspect according to any one of the preceding aspects, the resistance element includes a flow restrictor to restrict flow of medical fluid along the infusion line through resistance element.

In a $5^{th}$ aspect according to any one of the preceding aspects, the compliance element has an inlet port and an outlet port for the medical fluid and defines a portion of the medical fluid path.

In a $6^{th}$ aspect according to any one of the preceding aspects, the compliance element comprises a drip chamber.

In a $7^{th}$ aspect according to any one of the preceding aspects, the IV infusion set further comprises an additional drip chamber arranged downstream from the medical fluid source with respect to the direction of fluid flow along the infusion line from the medical fluid source towards the patient access. Optionally, the additional drip chamber is arranged upstream from the pump with respect to the direction of fluid flow along the infusion line from the medical fluid source towards the patient access.

In an $8^{th}$ aspect according to any one of the preceding aspects, the resistance element comprises a hollow body interposed along the infusion line to allow passage of the medical fluid, the hollow body having a fluid passage section smaller than a fluid passage section of the infusion line defining a section restriction for the medical fluid flow.

In a 9$^{th}$ aspect according to the preceding aspect, the hollow body defines a portion of the medical fluid path.

In a 10$^{th}$ aspect according to any one of the two preceding aspects, the hollow body includes a slender hollow body.

In an 11$^{th}$ aspect according to any one of the three preceding aspects, the hollow body is made of a material more rigid than the material of the infusion line. Alternatively or additionally to aspects 9 to 11, the hollow body has a longitudinal axis coincident with a longitudinal axis of the infusion line and a circular passage section smaller than a passage section of the infusion line.

In a 12$^{th}$ aspect according to any one of the preceding aspects, the resistance element is directly connected to an outlet of the compliance element.

In a 13$^{th}$ aspect according to any one of the preceding aspects, the resistance element comprises a needle. Optionally, the resistance element includes one of: a 16 G needle, an 18 G needle, a 20 G needle, a 22 G needle, a 24 G needle, and a 27 G needle.

In a 14$^{th}$ aspect according to any one of the preceding aspects, the IV infusion set further comprises a second resistance element.

In a 15$^{th}$ aspect according to the preceding aspect, the second resistance element is arranged on the infusion line upstream from the compliance element with respect to the direction of fluid flow along the infusion line from the medical fluid source towards the patient access.

In a 16$^{th}$ aspect according to any one of the preceding aspects, the second resistance element comprises a second hollow body interposed along the infusion line to allow passage of the medical fluid, the second hollow body having a fluid passage section smaller than a fluid passage section of the infusion line defining a section restriction for the medical fluid flow.

In a 17$^{th}$ aspect according to the preceding aspect, the second hollow body defines a portion of the medical fluid path.

In an 18$^{th}$ aspect according to any one of the two preceding aspects, the second hollow body includes a slender hollow body.

In a 19$^{th}$ aspect according to any one of the three preceding aspects, the second hollow body is made of a material more rigid than the material of the infusion line.

In a 20$^{th}$ aspect according to any one of the preceding aspects, the second resistance element is directly connected to an inlet of the compliance element.

In a 21$^{st}$ aspect according to any one of the preceding aspects in combination with aspect 14, the second resistance element comprises a needle. Optionally the second resistance element includes one of: a 16 G needle, an 18 G needle, a 20 G needle, a 22 G needle, a 24 G needle, and a 27 G needle.

In a 22$^{nd}$ aspect according to any one of the preceding aspects in combination with aspect 14, the second resistance element includes a flow restrictor.

In a 23$^{rd}$ aspect according to any one of the preceding aspects, the patient signal is indicative of any one of: a peripheral venous pressure, a heart rate of a patient, a respiratory rate of a patient.

In a 24$^{th}$ aspect according to any one of the preceding aspects, the pump is positive displacement pump configured to operate on the external of a tube portion of the infusion line to convey medical fluid along the direction of fluid flow. Optionally, the pump includes one of a peristaltic pump and a finger pump.

In a 25$^{th}$ aspect according to any one of the preceding aspects, the resistance element is arranged downstream from the pump with respect to the direction of fluid flow along the infusion line from the medical fluid source towards the patient access.

In a 26$^{th}$ aspect according to any one of the preceding aspects, the IV infusion set further comprises an attachment element placed in correspondence of the first end of the infusion line, the source of medical fluid comprising a container, the attachment element being configured to fluidly couple the infusion line with the container of medical fluid. Optionally, the container includes one of a bag and a bottle.

In a 27$^{th}$ aspect according to any one of the preceding aspects, the IV infusion set further comprises a flow regulator configured to selectively restrict a fluid flow passage inside the infusion line, said flow regulator being configured to progressively squeeze a portion of the infusion line thereby reducing the fluid flow passage. The fluid flow regulator is optionally configured to progressively squeeze a portion of the infusion line based on manual operation by a user.

In a 28$^{th}$ aspect according to any one of the preceding aspects, the infusion line includes a pressure coupling configured to be coupled and to cooperate with the sensor to allow the sensor to estimate the pressure signal.

In a 29$^{th}$ aspect according to the preceding aspect, the pressure coupling comprises a flat and elastic membrane configured to deform based on a pressure of the fluid flowing inside the infusion line.

In a 30$^{th}$ aspect according to the preceding aspect, the pressure coupling comprises a rigid body including an inlet port to receive an inlet tubing portion of the infusion line and an outlet port to receive an outlet tubing portion of the infusion line, the rigid body defining an inner housing divided by the flat and elastic membrane into a first chamber in fluid communication with both inlet and outlet port and a second air chamber isolated the first chamber.

In a 31$^{st}$ aspect according to any one of the preceding aspects, the sensor includes a transducer to detect a parameter indicative of a pressure signal along the infusion line and provide an electric signal function of the detected parameter.

In a 32$^{nd}$ aspect according to the preceding aspect, the sensor further includes a measurement module configured to receive the electric signal from the transducer and to determine the pressure signal based on the electric signal.

In a 33$^{rd}$ aspect according to any one of the preceding aspects, the sensor is coupled to an injection port.

In a 34$^{th}$ aspect according to the preceding aspect, the injection port comprises a first section in fluid communication with an internal volume of the infusion line, a second section including an external volume, the sensor being coupled to the external volume and configured to generate a secondary pressure signal based on a pressure in the external volume, and a membrane separating the first section from the second section. The control unit is configured to receive the secondary pressure signal and to determine the pressure signal based on the secondary pressure signal.

In a 35$^{th}$ independent aspect according to the invention there is provided an infusion line for medical fluid, the infusion line comprising at least one first end configured to connect to a source of medical fluid, at least one opposite second end configured to connect to a patient access, the infusion line defining a medical fluid path developing from the first end of the infusion line to the patient access, a compliance element configured to attenuate pressure variations of medical fluid in the infusion line, and a resistance element configured to reflect pressure waves moving along the infusion line. Based on a direction of fluid flow of the medical fluid through the infusion line from the first end towards the second end, the resistance element is arranged downstream from the compliance element and upstream the second end. Optionally, the infusion line includes a main infusion line and/or one or more auxiliary infusion lines connected to a main infusion line.

In a 36th aspect according to the preceding aspect, the infusion line further comprises a sensor configured to emit a signal indicative of a pressure of the medical fluid in the infusion line. The sensor is arranged downstream from the resistance element and upstream the second end.

In a 37th aspect according to any one of aspects 35 or 36, the resistance element includes a flow restrictor to restrict flow of medical fluid along the infusion line through resistance element.

In a 38th aspect according to any one of aspects 35 to 37, the compliance element has an inlet port and an outlet port for the medical fluid and defines a portion of the medical fluid path.

In a 39th aspect according to any one of aspects 35 to 38, the compliance element comprises a drip chamber.

In a 40th aspect according to any one of aspects 35 to 38, the infusion line further comprises an additional drip chamber arranged downstream from the first end with respect to the direction of fluid flow.

In a 41st aspect according to any one of aspects 35 to 40, the resistance element comprises a hollow body interposed along the infusion line to allow passage of the medical fluid, the hollow body having a fluid passage section smaller than a fluid passage section of the infusion line defining a section restriction for the medical fluid flow.

In a 42nd aspect according to the preceding aspect, the hollow body defines a portion of the medical fluid path.

In a 43rd aspect according to any one of aspects 41 or 42, the hollow body includes a slender hollow body.

In a 44th aspect according to any one of aspects 41 to 43, the hollow body is made of a material more rigid than the material of the infusion line.

In a 45th aspect according to any one of aspects 35 to 44, the resistance element is directly connected to an outlet of the compliance element.

In a 46th aspect according to any one of aspects 35 to 45, the resistance element comprises a needle. Optionally, the resistance element includes one of: a 16 G needle, an 18 G needle, a 20 G needle, a 22 G needle, a 24 G needle, and a 27 G needle.

In a 47th aspect according to any one of aspects 35 to 46, the infusion line further comprises a second resistance element.

In a 48th aspect according to the preceding aspect, the second resistance element is arranged on the infusion line upstream from the compliance element with respect to the direction of fluid flow along the infusion line.

In a 49th aspect according to any one of aspects 47 or 48, the second resistance element comprises a second hollow body interposed along the infusion line to allow passage of the medical fluid, the second hollow body having a fluid passage section smaller than a fluid passage section of the infusion line defining a section restriction for the medical fluid flow.

In a 50th aspect according to the preceding aspect, the second hollow body defines a portion of the medical fluid path.

In a 51st aspect according to any one of aspects 49 or 50, the second hollow body includes a slender hollow body.

In a 52nd aspect according to any one of aspects 49 to 51, the second hollow body is made of a material more rigid than the material of the infusion line.

In a 53rd aspect according to any one of aspects 35 to 52 in combination with aspect 47, the second resistance element is directly connected to an inlet of the compliance element.

In a 54th aspect according to any one of aspects 35 to 53 in combination with aspect 47, the second resistance element comprises a needle. Optionally, the second resistance element includes one of: a 22 G needle and a 27 G needle.

In a 55th aspect according to any one of aspects 35 to 54 in combination with aspect 47, the second resistance element includes a flow restrictor.

In a 56th aspect according to any one of aspects 35 to 55, the infusion line further comprises an attachment element placed in correspondence of the first end of the infusion line, the attachment element being configured to connect to a source of medical fluid comprising a container, the attachment element being configured to fluidly couple the infusion line with the container of medical fluid. Optionally, the container includes one of a bag and a bottle.

In a 57th aspect according to any one of aspects 35 to 56, the infusion line further comprises a flow regulator configured to selectively restrict a fluid flow passage inside the infusion line, the flow regulator being configured to progressively squeeze a portion of the infusion line thereby reducing the fluid flow passage. The fluid flow regulator is optionally configured to progressively squeeze a portion of the infusion line based on manual operation by a user.

In a 57th aspect according to any one of aspects 35 to 56 in combination with aspect 36, the infusion line includes a pressure coupling configured to be coupled and to cooperate with the sensor to allow the sensor to estimate the pressure signal.

In a 59th aspect according to the preceding aspect, the pressure coupling comprises a flat and elastic membrane configured to deform based on a pressure of the fluid flowing inside the infusion line.

In a 60th aspect according to the preceding aspect, the pressure coupling comprises a rigid body including an inlet port to receive an inlet tubing portion of the infusion line and an outlet port to receive an outlet tubing portion of the infusion line, the rigid body defining an inner housing divided by the flat and elastic membrane into a first chamber in fluid communication with both inlet and outlet port and a second air chamber isolated the first chamber.

In a 61st aspect according to any one of aspects 35 to 60 in combination with aspect 36, the sensor includes a transducer to detect a parameter indicative of a pressure signal along the infusion line and provide an electric signal function of the detected parameter.

In a 62nd aspect according to the preceding aspect, the sensor further includes a measurement module configured to receive the electric signal from the transducer and to determine the pressure signal based on the electric signal.

In a 63rd aspect according to any one of aspects 35 to 62 in combination with aspect 36, the sensor is coupled to an injection port.

In a 64th aspect according to the preceding aspect, the injection port comprises a first section in fluid communication with an internal volume of the infusion line, a second section including an external volume, the sensor being coupled to the external volume and configured to generate a secondary pressure signal based on a pressure in the external volume, and a membrane separating the first section from the second section. The control unit is configured to receive the secondary pressure signal and to determine the pressure signal based on the secondary pressure signal.

In a 65th independent aspect in accordance with the invention there is provided a process for detecting the pressure of a medical fluid in an IV infusion set, the IV infusion set being realized in accordance with any one of aspects 1 to 34 (including intermediate aspects), the process comprising controlling, by the control unit, the pump to convey medical fluid along the infusion line in the direction of fluid flow, receiving the pressure signal from the sensor, determining, by the control unit, the patient signal indicative of a vital signal of the patient based on the pressure signal.

In a 66th according to any one of the preceding aspects, the infusion line is made of a flexible material (or includes portions made of flexible material).

In a 67th according to any one of the preceding aspects, the infusion line is made of a bendable and/or squeezable plastic material.

In a 68th according to any one of the preceding aspects, the resistance element (130, 130-1, 130a, 130a-1) comprises a hollow body interposed along the infusion line (200) to allow passage of the medical fluid, the infusion line having a substantially circular fluid passage cross section and the hollow body having a fluid passage cross section smaller than the fluid passage cross section of the infusion line (200) defining a section restriction for the medical fluid flow, the hollow body defining an elongated portion of the medical fluid path.

In a 69th according to any one of the preceding aspects, the resistance element (130, 130-1, 130a, 130a-1) comprises a hollow body interposed along the infusion line (200) with an elongated fluid passage to allow passage of the medical fluid, the hollow body receiving fluid from a portion of the infusion line, conveying the fluid along the elongated fluid passage and delivering fluid to a subsequent portion of the infusion line, at least an inlet of, and preferably all, the elongated fluid passage having a fluid passage cross section smaller than a fluid passage cross section of the infusion line (200).

In a 70th aspect according to any one of the preceding aspects, the infusion line is (substantially or at least partly) transparent.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will now follow, with reference to the appended figures, provided by way of non-limiting example, in which.

DETAILED DESCRIPTION

Figure 1A:
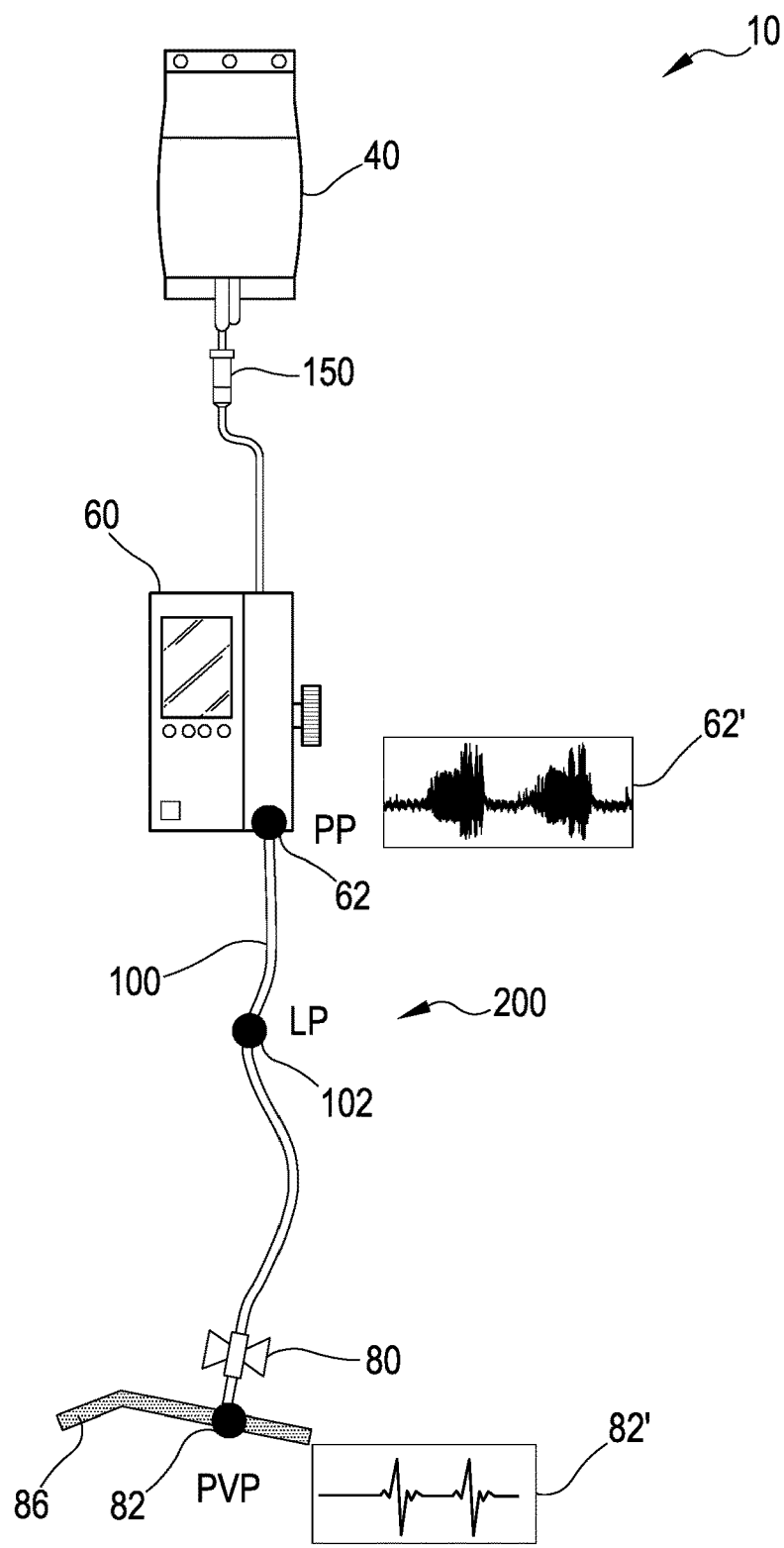
FIG. 1A schematically shows a first known IV infusion set.

FIG. 1A schematically shows a first known IV infusion set 10. The IV infusion set 10 includes a source 40 of medical fluid, a drip chamber 150, an infusion apparatus 60 including an infusion pump 62, an infusion line 200 including a main infusion line 100, and a patient access 80. The patient access 80 typically comprises a cannula configured to provide access to the cardiovascular system 86 of a patient.

In accordance with embodiments of the present invention, an infusion line 200 may include a main infusion line 100 and, optionally, one or more auxiliary infusion lines 100a. The term "infusion line 200" is, thus, understood to encompass all combinations including a main infusion line 100 only and all combinations of a main infusion line 100 with one or more auxiliary infusion lines 100a. For example, a set of a main infusion line 100 in combination with three auxiliary infusion lines 100a may, thus, be collectively referred to as "infusion line 200".

During operation of the infusion apparatus 60, medical fluid is supplied from the source 40 of medical fluid through main infusion line 100 towards patient access 80, where it is infused into the patient's cardiovascular system 86. The medical fluid is conveyed using a pump 62, for example a peristaltic pump, typically integrated into the infusion apparatus 60. Main infusion line 100 may be provided, for example at position LP, with a pressure sensor 102 configured to detect a pressure of fluid present within main infusion line 100.

FIG. 1A further illustrates effects that typically occur during operation of the IV infusion set 10. Diagram 62' illustrates a pressure signal typically observable downstream from the pump, for example at position PP (denoted as "PP" for "pump pressure") on main infusion line 100. At position PP, a pressure signal taken from a pressure sensor may generally correspond to the signal illustrated in diagram 62'. The pressure signal shown in diagram 62' is indicative of the pressure in main infusion line 100 at position PP and may suffer from disturbances caused by operation of the pump 62 upstream from or approximately at position PP.

The patient venous pressure (PVP) is present within the cardiovascular system 86 of a patient. An example signal indicative of the PVP is illustrated in diagram 82'. It is desired to measure the PVP within the main infusion line 100, for example at position LP (denoted as "LP" for "line pressure"). However, the effective pressure signal that can be obtained at position LP is typically affected both by disturbances caused by the pump (as shown in diagram 62') and propagating downstream from position PP towards position LP, as well as by the actual PVP signal present within the cardiovascular system 86 of a patient and propagating upstream from the patient access 80 towards position LP. The terms "upstream" and "downstream" are defined by a direction of fluid flow of medical fluid during operation of infusion apparatus 60, namely generally from the source 40 of medical fluid towards the patient access 80.

Figure 1B:
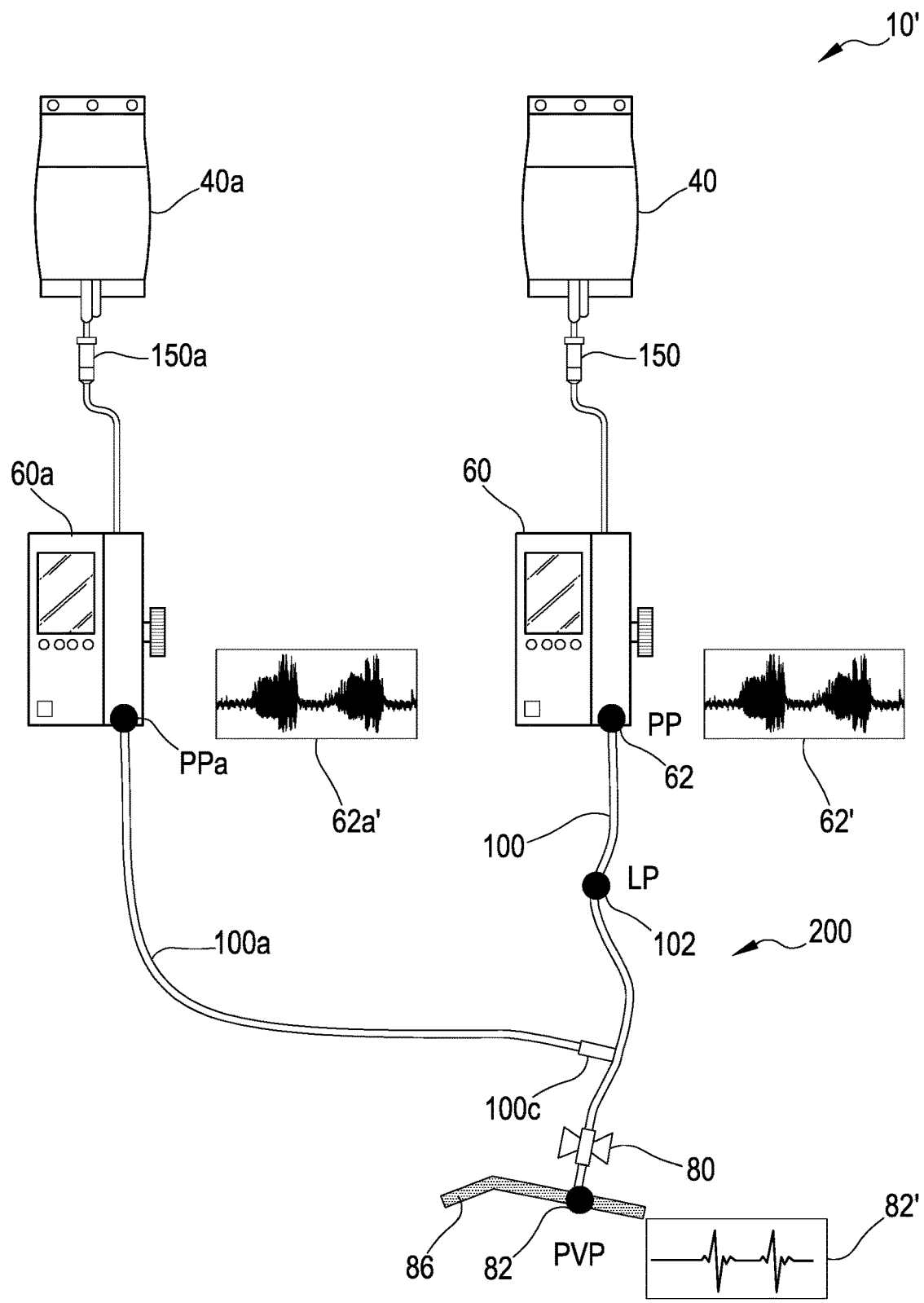
FIG. 1B schematically shows a second known IV infusion set including a main infusion line and an auxiliary infusion line.

FIG. 1B schematically shows a second known IV infusion set 10' having an infusion line 200 including a main infusion line 100 and an auxiliary infusion line 100a. The IV infusion set 10' includes, on the main infusion line 100, a source 40 of medical fluid, a drip chamber 150, an infusion apparatus 60 including an infusion pump 62, and a patient access 80. The patient access 80 typically comprises a cannula configured to provide access to the cardiovascular system 86 of a patient. The IV infusion set 10' further includes, on an auxiliary infusion line 100a, an auxiliary source 40a of medical fluid, an auxiliary drip chamber 150a, and an auxiliary infusion apparatus 60a including an auxiliary infusion pump 62a. The auxiliary infusion line 100a is connected to the main infusion line 100 by an infusion line connector 100c (e.g. a Luer connector), the connection being realized along the main infusion line 100 between the patient access 80 and the infusion pump 62, typically proximate the patient access 80.

During operation of infusion apparatuses 60 and/or 60a, medical fluid is supplied from one or both of sources 40 and 40a of medical fluid through main infusion line 100 and/or auxiliary infusion line 100a towards patient access 80, where it is infused into the patient's cardiovascular system 86. The medical fluid is conveyed using pumps 62 and/or 62a (e.g. either or both including a peristaltic pump), typically integrated into the infusion apparatuses 60 and/or 60a. Similar to main infusion line 100, auxiliary infusion line 100a may be provided, for example at position LPa, with a pressure sensor 102a configured to detect a pressure of fluid present within infusion line 100a.

FIG. 1B further illustrates effects that typically occur during operation of the IV infusion set 10'. Diagrams 62' and 62a' illustrate corresponding pressure signals typically observable downstream from the respective pumps 62 and 62a, for example at positions PP (denoted as "PP" for "pump pressure") and PPa (denoted as "PPa" for "auxiliary pump pressure") on main/auxiliary infusion lines 100 and 100a. At position PP, a pressure signal taken from a pressure sensor may generally correspond to the signal illustrated in diagram 62'. The pressure signal shown in diagram 62' is indicative of the pressure in main infusion line 100 at position PP and may suffer from disturbances caused by operation of the pump 62 upstream from or approximately at position PP. Similarly, at position PPa, a pressure signal taken from a pressure sensor may generally correspond to the signal illustrated in diagram 62a'. The pressure signal shown in diagram 62a' is indicative of the pressure in auxiliary infusion line 100a at position PPa and may similarly suffer from disturbances caused by operation of the pump 62a upstream from or approximately at position PPa.

Again, an example signal indicative of the PVP is illustrated in diagram 82'. As described above with respect to FIG. 1A, it is desired to measure the PVP within the main infusion line 100, for example at position LP (denoted as "LP" for "line pressure"), or within the auxiliary infusion line 100a, for example at position LPa (denoted as "LPa" for "auxiliary line pressure"). However, the effective pressure signal that can be obtained at positions LP and/or LPa is typically affected both by disturbances caused by the pumps 62 and/or 62a (as shown in diagrams 62' and 62a') and propagating downstream from positions PP and/or PPa, respectively, towards positions LP and/or LPa, respectively, as well as by the actual PVP signal present within the cardiovascular system 86 of a patient and propagating upstream from the patient access 80 towards positions LP and LPa. The terms "upstream" and "downstream" are defined as described above. In case of auxiliary infusion line 100a, these terms are defined by a direction of fluid flow of medical fluid during operation of auxiliary infusion apparatus 60a, namely generally from the auxiliary source 40a of medical fluid towards the patient access 80.

Figure 2:
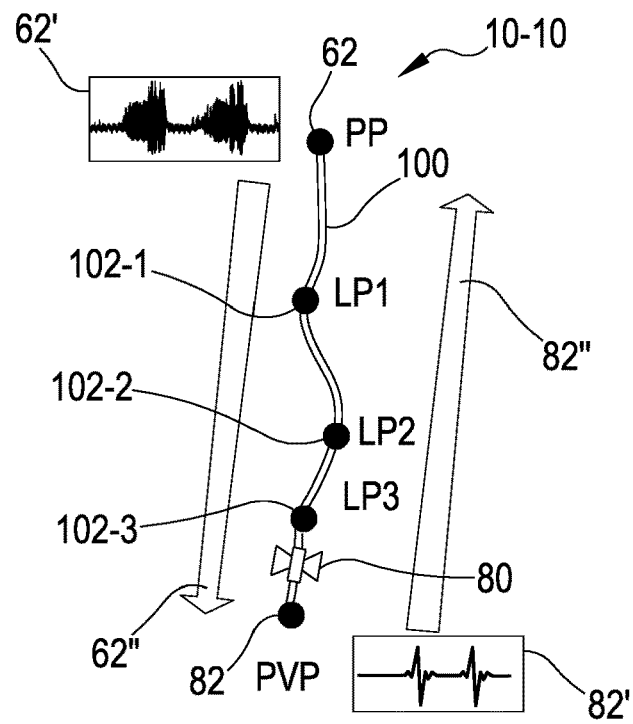
FIG. 2 schematically shows a known IV infusion set and illustrates effects that may occur during measurement of line pressure in an IV infusion line in accordance with prior art designs.

FIG. 2 schematically shows a known IV infusion set 10-10 and illustrates effects that may occur during measurement of line pressure LP in a main infusion line 100 in accordance with prior art designs. For illustration purposes, several positions LP1, LP2, or LP3 are shown in FIG. 2. At any one of these positions LP1, LP2, or LP3, a pressure sensor 102-1, 102-2, or 102-3 could be placed in order to measure the LP at one of there positions. The reason for selecting different positions, for example positions LP1, LP2, or LP3 as shown in FIG. 2, or other positions, is that a number of factors affect the quality of potential pressure measurements along main infusion line 100.

For example, the compliance of main infusion line 100 itself influences the manner in which both the pump signal amplitude spectrum and PVP propagate through main infusion line 100. Further, pressure wave reflections can occur at several components, for example at infusion apparatus 60 and/or at patient access 80. Such reflections may amplify the pump signal amplitude spectrum and/or introduce artifacts potentially deteriorating the pressure signal to be measured. Further, the pump signal amplitude spectrum greatly depends upon an operating speed of the pump 62 and may show resonances at a plurality of frequencies. These resonances may also depend on the compliance of main infusion line 100. Additionally, pressure waves transmitted along main infusion line 100 may, depending upon their frequency and/or amplitude, may either amplify each other or cancel each other out. Several additional effects exist, so that measuring PVP at any one of positions LP1, LP2, or LP3 may or may not produce a signal having sufficient quality in order to reliably obtain a signal indicative of PVP therefrom. Identifying a suitable position for measuring PVP is, thus, typically complex, error-prone, and/or not reliably reproducible.

Generally, pressure waves typically lose energy while propagating along main infusion line 100. This is illustrated in FIG. 2 by arrows 62" and 82". Pressure waves caused by the pump 62, for example, travel downstream along main infusion line 100, i.e. in direction 62", and the amplitude of these pressure waves decreases, inter alia depending upon attenuation properties of main infusion line 100. Similarly, pressure waves originating from the cardiovascular system of a patient, travel upstream along main infusion line 100, i.e. in direction 82", and the amplitude of these pressure waves decreases along main infusion line 100.

However, due to the many factors described above, it is not sufficient to move the position LP as much as possible into the direction of patient access 80, for example into position LP-3, in order to obtain a pressure signal of sufficient quality. As such, the placement of a sensor in order to obtain a pressure signal indicative of PVP remains problematic.

Figure 2A:
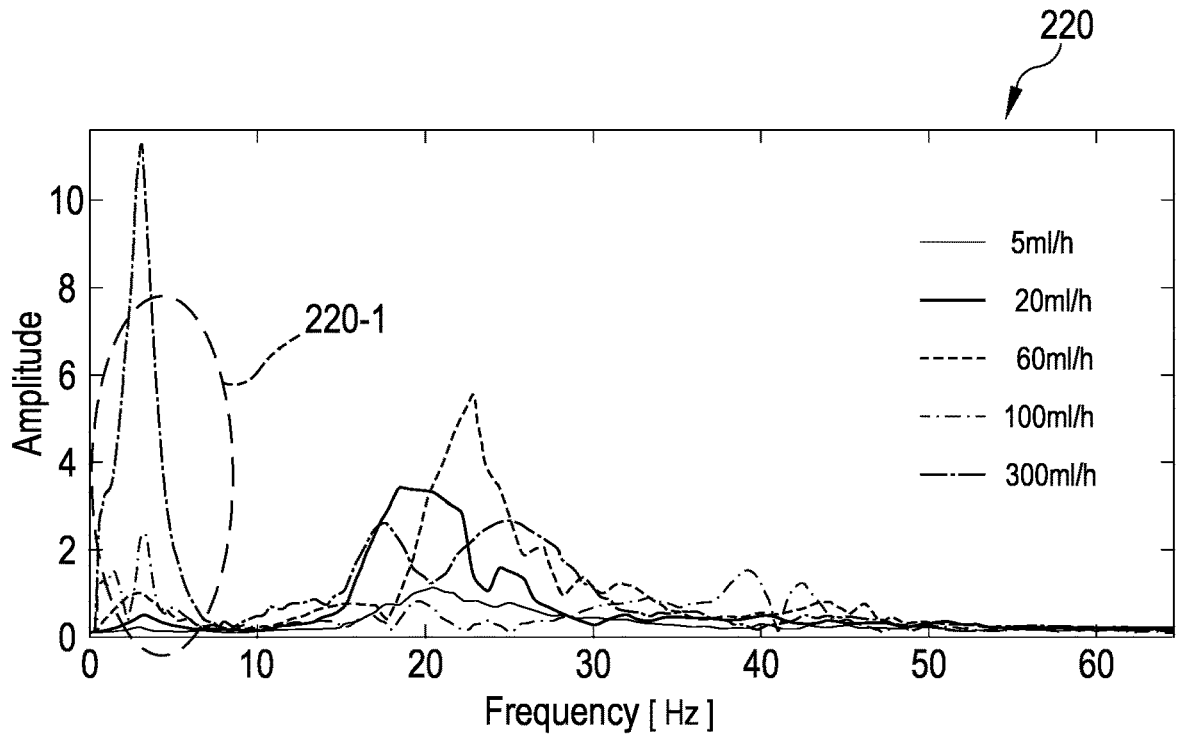
FIG. 2A shows a diagram illustrating frequency/amplitude for different flow rates.

FIG. 2A shows a diagram 220 illustrating frequency/amplitude for different flow rates. The graphs shown in FIG. 2A represent respective signal amplitude spectra (derived using Fast Fourier Transformations (FFT)) of a signal indicative of pump pressure, the signal including the pump signal amplitude spectrum, as measured in a fluid line on which pump 62 operates. The measurements were made based on an IV infusion set corresponding to IV infusion set 10-10 as schematically shown in FIG. 2 and largely corresponding to IV infusion set 10 as shown in FIG. 1A. Water was used as the medical fluid and the sensor used in performing the measurements was a UC3-E1JABCCBGA1G sensor available from Endress+Hauser Messtechnik GmbH+Co. KG, Germany.

As mentioned above, pump signal amplitude spectrum form greatly depends upon the operating speed of the pump 62 and may show resonances at a plurality of frequencies. Such resonances are illustrated in diagram 220 shown in FIG. 2A. Diagram 220 shows several graphs indicative of respective amplitudes of the pump pressure signal at different pump flow rates, namely at 5 ml/h, at 20 ml/h, at 60 ml/h, at 100 ml/h, and at 300 ml/h. Particularly powerful amplitudes occur below 5 Hz (at 300 ml/h) and around 20 Hz (at 60 ml/h).

Generally, the behavior of the pump 62 can be roughly divided in 3 infusion flow bands. The first band ranges from 0 ml/h to 60 ml/h and results in frequencies mainly between 12 Hz to 50 Hz. The second band ranges from 60 ml/h to 200 ml/h and results in frequencies mainly between 0 Hz to 6 Hz as well as 12 Hz to 50 Hz. The second band, thus, shows a mixed behavior. The third band includes fluid flow greater than 200 ml/h and results in frequencies mainly between 0 Hz to 6 Hz.

Figure 2B:
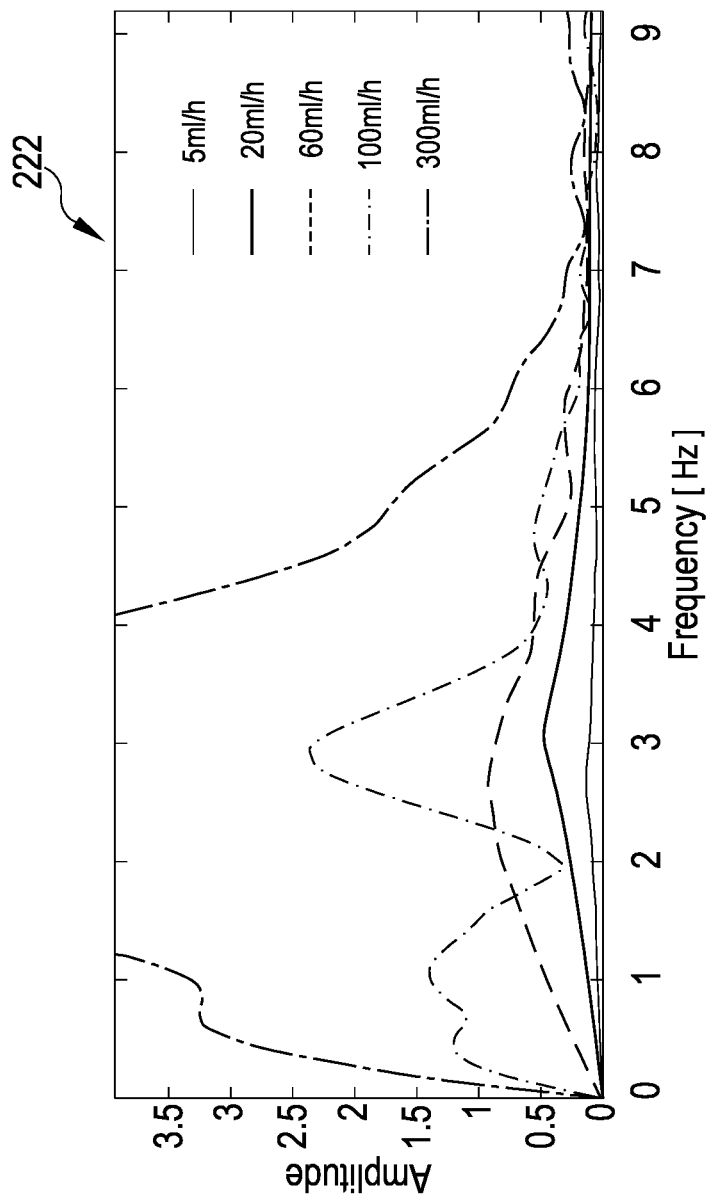
FIG. 2B shows a diagram illustrating frequency/amplitude for different flow rates.

FIG. 2B shows a diagram 222 illustrating frequency/amplitude for different flow rates. Diagram 222 illustrates the amplitude of the pump pressure signal in a more narrow frequency band (e.g. below 8 Hz). The frequency of patient vital signals, for example the heart beat of a patient, is typically observed at frequencies around 1 Hz. Therefore, the frequency band shown in FIG. 2B is of particular interest. Again, it can be seen that especially for higher flow rates (e.g. 10 ml/h or higher) the pump signal spectrum has a peak at frequencies of, for example, around 1 Hz and around 3 Hz. Therefore, measurements of patient vital signals are increasingly difficult to take at such higher flow rates.

Figure 3:
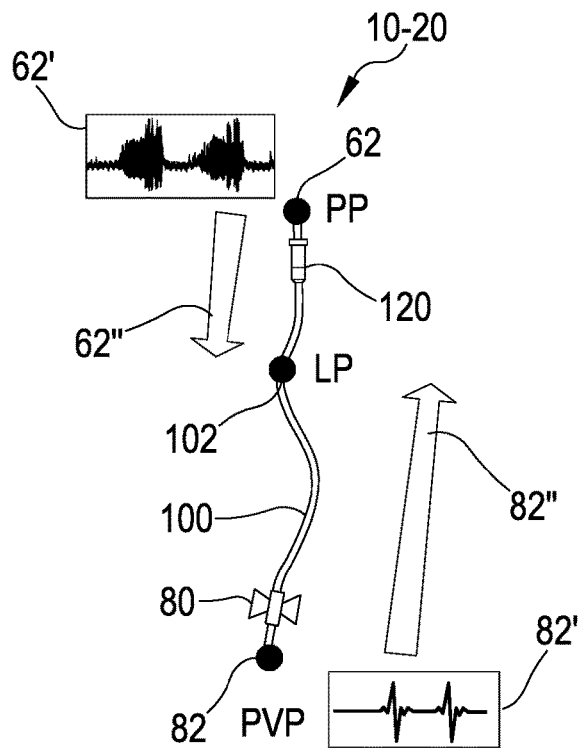
FIG. 3 schematically shows a known IV infusion set and illustrates effects that may occur during measurement of line pressure in an IV infusion line in accordance with prior art designs.

FIG. 3 schematically shows a known IV infusion set 10-20 and illustrates effects that may occur during measurement of line pressure in an IV infusion line in accordance with prior art designs. The overall structure of IV infusion set 10-20 is largely identical to that of IV infusion set 10-10 as shown in FIG. 2. However, a compliance element 120 (e.g. a drip chamber) has been added to main infusion line 100 of IV infusion set 10-20 upstream from a position LP at which line pressure LP is to be measured (or downstream from the pump 62).

Also in the IV infusion set 10-20, pressure waves typically lose energy while propagating along main infusion line 100 as described above with respect to FIG. 2. Therefore, this is also illustrated in FIG. 3 by arrows 62" and 82". Pressure waves caused by the pump 62, for example, travel downstream along main infusion line 100, i.e. in direction 62", and the amplitude of these pressure waves decreases, inter alia depending upon attenuation properties of main infusion line 100. Similarly, pressure waves originating from the cardiovascular system of a patient, travel upstream along main infusion line 100, i.e. in direction 82", and the amplitude of these pressure waves decreases along main infusion line 100.

The drip chamber arranged upstream position LP acts as a compliance element 120, effectively dampening or attenuating the pressure propagating along main infusion line 100. However, the compliance element 120 not only attenuates pressure propagating downstream, for example unwanted pump signal spectrum components, but also pressure propagating upstream, for example PVP. This effect is illustrated in the diagrams shown in FIGS. 3A and 3B.

Figure 3A:
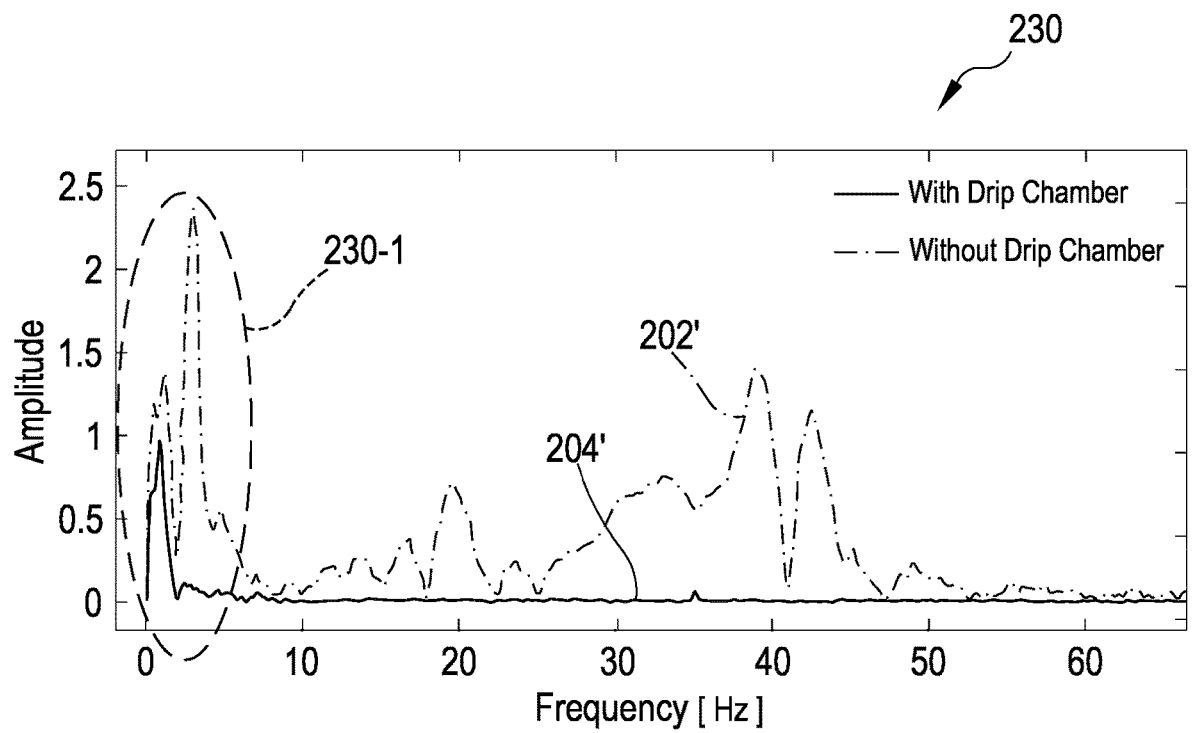
FIG. 3A shows a diagram illustrating frequency/amplitude occurring in IV infusion sets with and without drip chamber.

FIG. 3A shows a diagram 230 illustrating frequency/amplitude occurring in IV infusion sets with (IV infusion set 10-20) and without (IV infusion set 10-20) a drip chamber. Diagram 230 shows the frequency spectrum of a pump pressure signal, wherein graph 202' illustrates the frequency spectrum for an IV infusion set 10-10 without a compliance element 120 (e.g. without a drip chamber) and wherein graph 204' illustrates the frequency spectrum for an IV infusion set 10-20 provided with a compliance element 120. In the example shown, the pump 62 was operated at a speed of 100 ml/h. As can be seen from graphs 202' and 204', the compliance element 120 practically eliminates frequencies above 10 Hz and substantially reduces frequencies below 10

Hz. This is a desired behavior in terms of reducing unwanted pump signal spectrum components with respect to improving the signal/noise ratio.

Figure 3B:
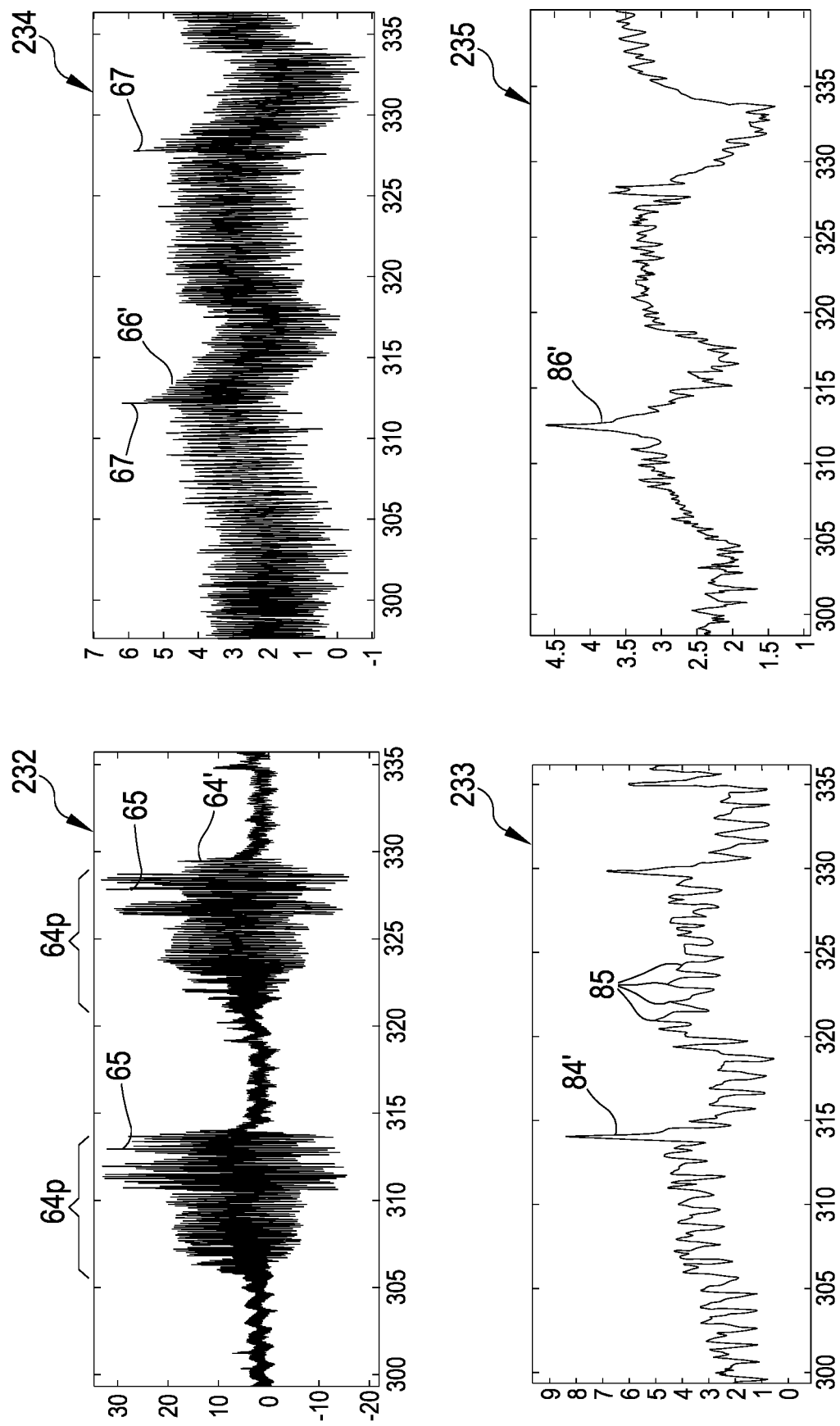
FIG. 3B shows several diagrams respectively illustrating example signals indicative of pump pressure and patient venous pressure.

FIG. 3B shows several diagrams 232, 233, 234, and 235 respectively illustrating example signals indicative of pump pressure and patient venous pressure (signals 64', 66', 84', and 86'). Diagrams 232, 233, 234, and 235 show an absolute pressure (mmHg) on the vertical axes and time (seconds) on the horizontal axes. It is noted that diagrams 232 and 234, as wells as diagrams 233 and 235, show different ranges of pressure (e.g. about −20 mmHg to about 30 mmHg in diagram 232 as compared to about −1 mmHg to about 7 mmHg in diagram 234).

Diagrams 232 and 233 show signals acquired based on an IV infusion set 10-10 without a compliance element 120 (e.g. a drip chamber). Diagrams 234 and 235 show signals acquired based on an IV infusion set 10-20 provided with a compliance element 120. In both examples, pump 62 was operated at a speed of 60 ml/h.

It can be seen from diagram 232 that signal 64' contains regions 64p exhibiting substantial pump signal spectrum components as the activity of pump 62 manifests itself in the form of a regularly recurring increases of amplitude (see regions 64p). Within such regions 64p, pump signal spectrum components typically peaks, for example at or around positions 65.

Diagram 233 illustrates a signal 84' which has been obtained by applying a 3 Hz low pass filter to signal 64' shown in diagram 232. As can be seen, signal 84' contains much less unwanted pump signal spectrum components but still contains, by way of example, two peaks caused by the operation of the pump 62. Apparently, therefore, substantial portions of unwanted pump signal spectrum components occur at frequencies above 3 Hz. Further, signal 84' shows a series of peaks 85 indicative of corresponding heart pulses.

As can be seen from diagram 234, in the example, the presence of a compliance element 120 results in signal 66' being attenuated significantly, approximately by a factor of 8 (see different pressure ranges in diagrams 232 and 234). Exemplary signal 66' also exhibits two peaks at or around positions 67, indicating pump operation. However, the overall signal 86' appears to be substantially attenuated and the peaks appear less pronounced.

Diagram 235 once again shows a signal 86' obtained by applying a 3 Hz low pass filter to signal 66'. As can be seen from diagram 235, the resulting signal 86' is not only attenuated, but the previously clearly visible peaks 85 (see diagram 233) have mostly disappeared, even though peaks indicative of pump operation are still clearly distinguishable at or around the same time points as those of positions 67 in diagram 234 (see, approximately, at 312 seconds and at 328 seconds, respectively).

The diagrams shown in FIG. 3B, thus, demonstrate that a compliance element 120 present in an IV infusion set such as IV infusion set 10-20 (see FIG. 3) not only attenuates unwanted pump signal spectrum components, but also contributes to a significant and unwanted deterioration of the PVP signal. Therefore, the amplitude ratio is more favorable for heart signal detection based on the measured PVP, if a compliance element 120 is not present in the IV infusion set.

Figure 3C:
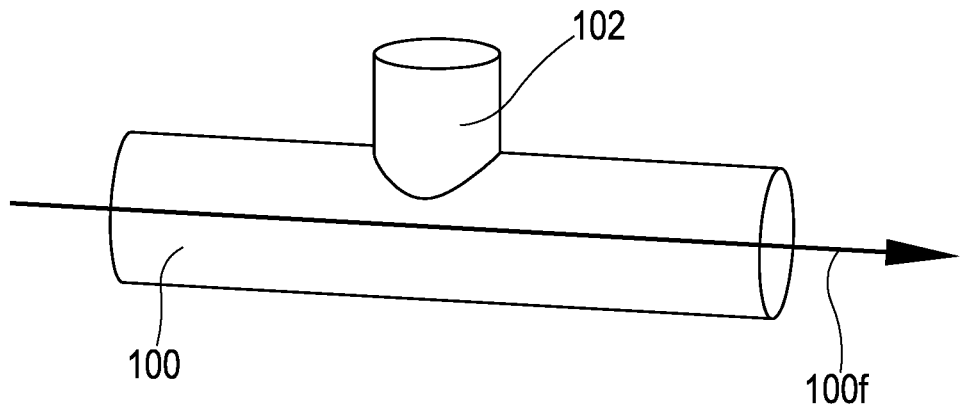
FIGS. 3C and 3D show prior art designs for placing a sensor on an IV infusion line.
Figure 3D:
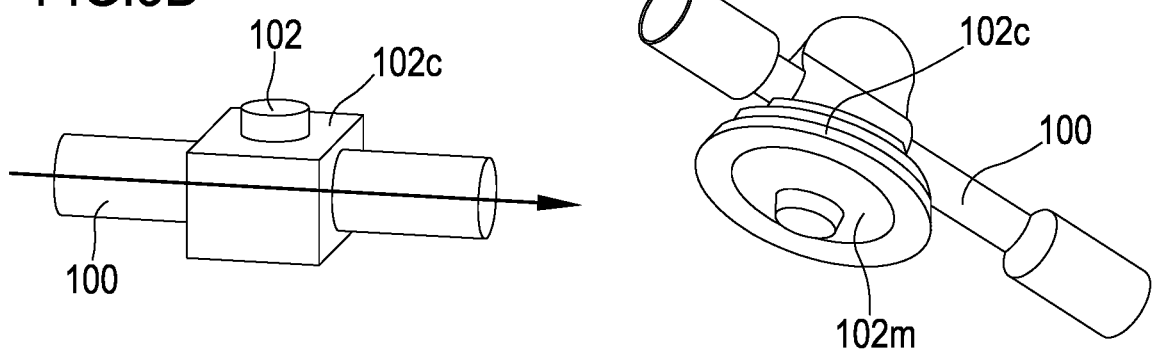
Figure 3E:
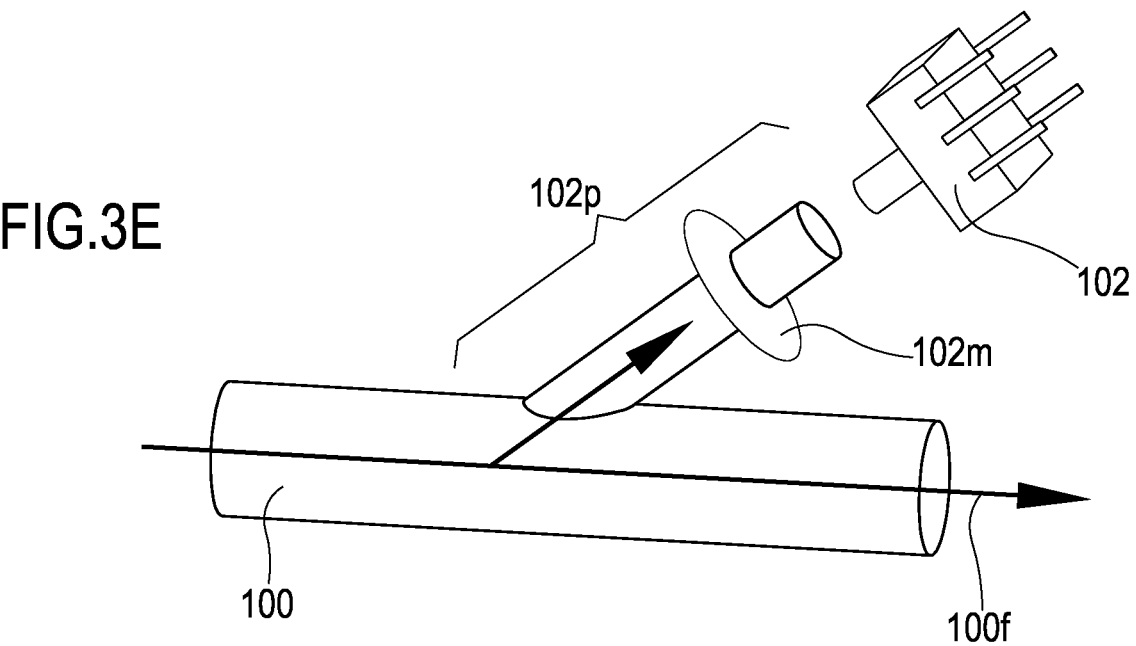
FIG. 3E schematically shows the placement of a sensor configured to measure the pressure of a fluid in an IV infusion line in accordance with embodiments of the present invention.

FIGS. 3C and 3D show some newly proposed designs for placing a sensor 102, 102a on an infusion line 100, 100a. What is shown in FIGS. 3C to 3E is applicable to infusion lines in general, for example infusion lines 100 and 100a, and to sensors in general, for example sensors 102 and 102a, even though the figures show an example based on line 100 and sensor 102. It is understood that the examples are applicable to any infusion lines and sensors described herein. FIG. 3C shows a sensor 102 directly connected to an IV infusion line 100. The internal pressure in infusion line 100 can be detected by measuring a physical property of the line during operation and by determining the internal pressure based on such physical property. In some examples, the physical property includes a force exerted by the fluid flowing through infusion line 100 upon an internal surface of the tubing, thereby resulting in pressure being transmitted to an external surface of the tubing, where the pressure (e.g. caused by deformation of the tubing) can be measured by a pressure-sensitive sensor. Pressure-sensitive sensors include, for example, piezoelectric sensors or other force-sensitive sensors. In other examples, the physical property includes vibrations exerted by the fluid flowing through infusion line 100 upon an internal surface of the tubing, thereby resulting in vibrations being transmitted to an external surface of the tubing, where the vibrations (e.g. caused by deformation and/or movement of the tubing) can be measured by a vibration-sensitive sensor. Vibration-sensitive sensors include, for example, microphone-based sensors or accelerometer-based sensors (e.g. sensors based on micro-electromechanical systems or MEMS).

FIG. 3D shows a sensor 102 connected to an IV infusion line 100 via a coupling membrane or a POD membrane. The internal pressure in infusion line 100 can be detected by measuring a physical property of the line during operation and by determining the internal pressure based on such physical property. In this example, the physical property includes wanted deformation of the IV infusion line 100, which is transmitted to a flat and elastic surface or membrane. In case of a POD membrane, the membrane may be part of a small chamber 102c to which a pressure-sensitive sensor may be coupled. In other cases, a pressure-sensitive sensor could be coupled directly to the membrane. An internal pressure of a fluid flowing though IV infusion line 100 may, thus, be measured based on a pressure exerted upon and transmitted by the membrane. In case of a POD-based sensor arrangement, the pressure is further transmitted to the small chamber, the pressure within which may be measured by a corresponding pressure-sensitive sensor coupled to the small chamber. On the left of FIG. 3D, a schematic representation of a sensor 102 connected to an infusion line 100 is shown, while on the right, a concrete example of a pressure POD including a chamber 102c and a membrane 102m is shown.

FIG. 3E schematically shows the placement of a sensor 102 configured to measure the pressure of a fluid in an IV infusion line 100 in accordance with embodiments of the present invention. In contrast to the sensor arrangements described in connection with FIGS. 3C and 3D, the arrangement shown in FIG. 3E is based on coupling a sensor to an injection port 102p, such as can typically be found in IV infusion lines 100. In order to measure an internal pressure of fluid flowing through IV infusion line 100, a membrane 102m positioned in injection port 102p separates a first section of injection port 102p, which is in fluid communication with an internal volume within IV infusion line 100 from a second section defining an external volume (e.g. containing air).

An internal pressure of fluid flowing through IV infusion line 100 exerts a corresponding pressure on membrane 102m, which in turn transmits the pressure to the second section of injection port 102p. A pressure-sensitive sensor 102 coupled to the second section (e.g. coupled to the external volume of air) may, thus, determine the internal pressure of fluid flowing through IV infusion line 100 based on a pressure within the external volume. The sensor arrangement shown in FIG. 3E may entail the advantage that an injection port may be used in order to determine an internal pressure of fluid flowing through IV infusion line 100, without requiring additional components (e.g. such as described with respect to FIGS. 3C and/or 3D).

Figure 4:
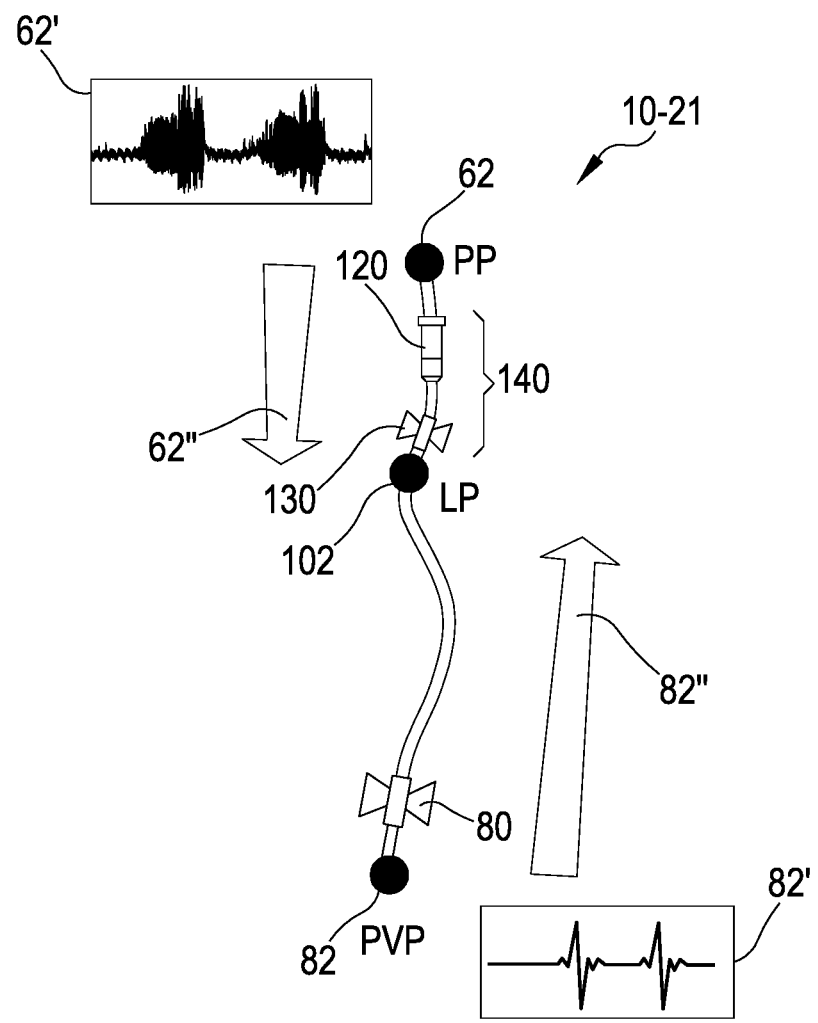
FIG. 4 schematically shows an IV infusion set in accordance with a first embodiment of the present invention.

FIG. 4 schematically shows an IV infusion set 10-21 in accordance with a first embodiment of the present invention. The overall structure of IV infusion set 10-21 is largely identical to that of IV infusion set 10-20 as shown in FIG. 3. However, a compliance element 120 (e.g. a drip chamber) has been added to main infusion line 100 of IV infusion set 10-21 upstream from a position LP at which line pressure LP is to be measured (or downstream from the pump 62). Further, a resistance element 130 (e.g. a cannula/needle 16 G to 27 G) has been added to main infusion line 100 of IV infusion set 10-21 upstream from the position LP at which line pressure LP is to be measured and downstream from compliance element 120. Compliance element 120 and resistance element 130 in combination may collectively be referred to as a damping element (see, e.g., damping elements 140, 140a in FIGS. 7 and 8). This document describes several possible combinations of a compliance element (e.g. compliance element 120) with one or more resistance elements (e.g. resistance elements 130, 130-1). Whenever a damping element 140 and/or 140a is referred to, any one of the several different combinations of compliance and resistance element(s) are applicable. Generally however, the damping element includes at least an upstream compliance element 120 and a downstream resistance element 130. It is noted that in the drawings, either separate elements (e.g. 120, 130, 130-1; see, e.g., FIGS. 4, 5) may be shown, or a combined element (e.g. 140, 140a; see, e.g., FIGS. 7, 8).

It is noted that, throughout the embodiments and where applicable, a compliance element of a damping element 140a arranged on the auxiliary infusion line 100a may be referred to as compliance element 120a (e.g. in order to distinguish from another compliance element 120 not arranged on the auxiliary infusion line 100a). Similarly, a resistance element of a damping element 140a arranged on the auxiliary infusion line 100a may be referred to as resistance element 130a or 130a-1 (e.g. in order to distinguish from another resistance element 130 or 130-1 not arranged on the auxiliary infusion line 100a).

As described above, and also with respect to the IV infusion set 10-21, pressure waves lose energy while propagating along main infusion line 100 as described above with respect to FIGS. 2 and 3. This is also illustrated in FIG. 4 by arrows 62" and 82".

The compliance element 120 arranged upstream position LP dampens or attenuates the pressure propagating along main infusion line 100. Further, resistance element 130 reflects pressure propagating along main infusion line 100, thus effectively acting as an amplifier of such pressure. Therefore, the compliance element 120 and the resistance element 130 in combination serve to reduce unwanted pump signal spectrum components and to amplify PVP with respect to position LP. Corresponding effects on the measured signals are shown in FIGS. 4A to 4D.

The resistance element 130 may include a hollow body interposed along main infusion line 100. The hollow body is configured to allow passage of the medical fluid and has a fluid passage section smaller than a fluid passage section of main infusion line 100. The hollow body, thus, defines a section restriction for the medical fluid flow. The hollow body may further define a portion of a medical fluid path developing from a first end of the infusion line to the patient access. In some embodiments, the hollow body includes a slender hollow body. The hollow body may be made of a material more rigid than the material of main infusion line 100. In some embodiments, the resistance element 130 may be directly connected to an outlet of the compliance element 120. The resistance element 130 may include a needle, for example any one of a 16 G needle, an 18 G needle, a 20 G needle, a 22 G needle, a 24 G needle, or a 27 G needle, depending upon desired resistance properties and/or a desired (maximum) flow rate.

The resistance element may be configured to reflect pressure waves propagating in fluid flow through main infusion line 100. In some embodiments the resistance element may be configured to primarily reflect pressure waves in fluid flow having frequencies substantially below 3 Hz, preferably ranging from 0.5 Hz to 3 Hz.

Figure 4A:
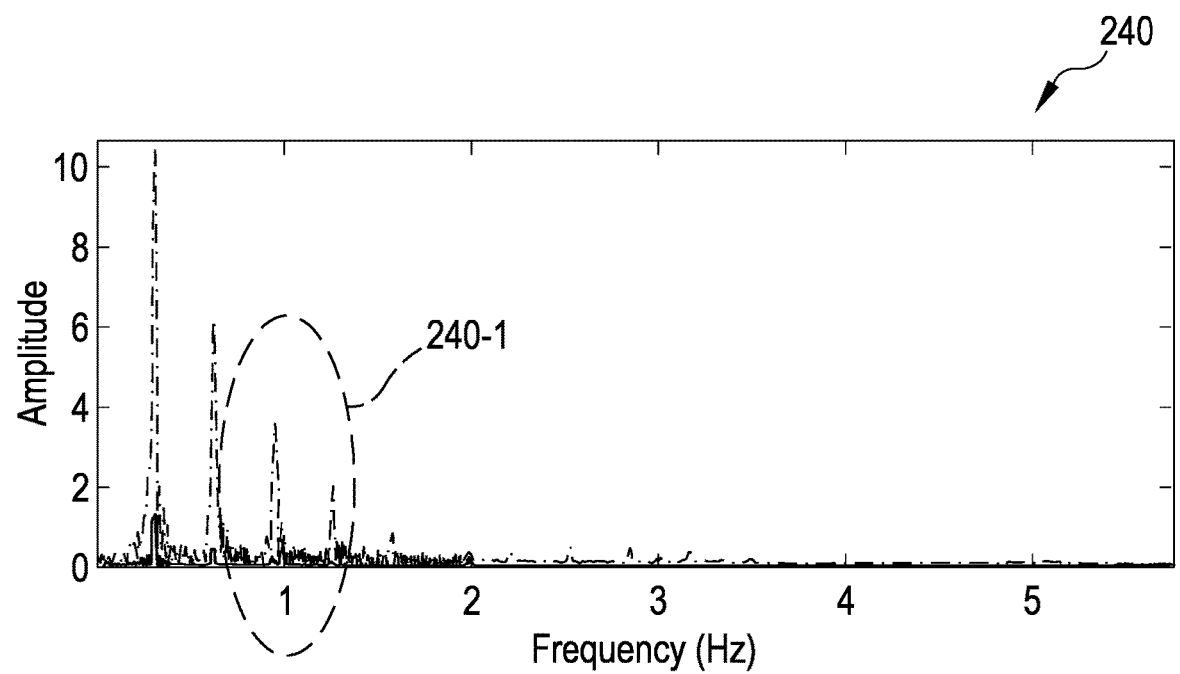
FIG. 4A shows a diagram illustrating frequency/amplitude occurring in prior art IV infusion sets as compared to IV infusion sets in accordance with the present invention.
Figure 4B:
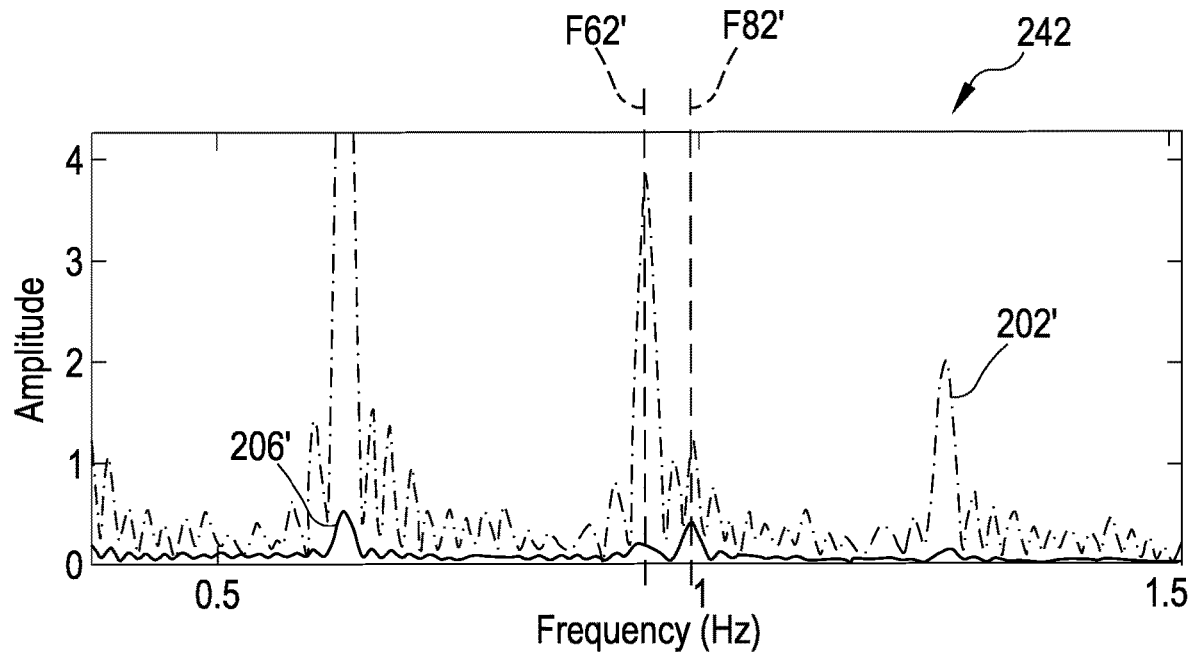
FIG. 4B shows a diagram illustrating frequency/amplitude occurring in prior art IV infusion sets as compared to IV infusion sets in accordance with the present invention.

FIGS. 4A and 4B respectively show diagrams 240 and 242 illustrating frequency/amplitude occurring in prior art IV infusion sets as compared to IV infusion sets in accordance with the present invention. FIG. 4A shows diagram 240 illustrating the frequency spectrum of pump pressure and PVP for a prior art IV infusion set 10-10 and for an IV infusion set 10-21 in accordance with the present invention. The example was based on a pump rate of 100 ml/h. Diagram 240 shows a larger frequency spectrum of 0 Hz to about 5 Hz, of which a frequency spectrum of 0.5 Hz to 1.5 Hz is most relevant for continuously measuring PVP in an IV infusion set. FIG. 4B, thus shows diagram 242 illustrating this relevant frequency spectrum of 0.5 Hz to 1.5 Hz as indicated in FIG. 240 by region 240-1.

FIG. 242 shows graph 202' indicative of the frequency spectrum of both pump pressure and PVP as measured in the prior art IV infusion set 10-10 and graph 206' indicative of the frequency spectrum as measured in the IV infusion set 10-21 in accordance with the firs embodiment shown in FIG. 4. As can be seen, the pump frequency spectrum is attenuated for all frequencies in the IV infusion set 10-21. Graph 202' exhibits several peaks having a much higher magnitude than those of graph 206'. The $1^{st}$ harmonic of the heart pulse is located at 1 Hz (see dashed line F82'), near a significant peak of the pump signal (slightly below 1 Hz).

As can be seen, the pump signal is much stronger than the heart signal in graph 202', while in graph 206' the pump signal is still slightly stronger than the heart signal, but exhibits a more similar magnitude. Therefore, the amplitude ratio is much more favorable in graph 206' and facilitates more accurate and more reliable measurements.

Figure 4C:
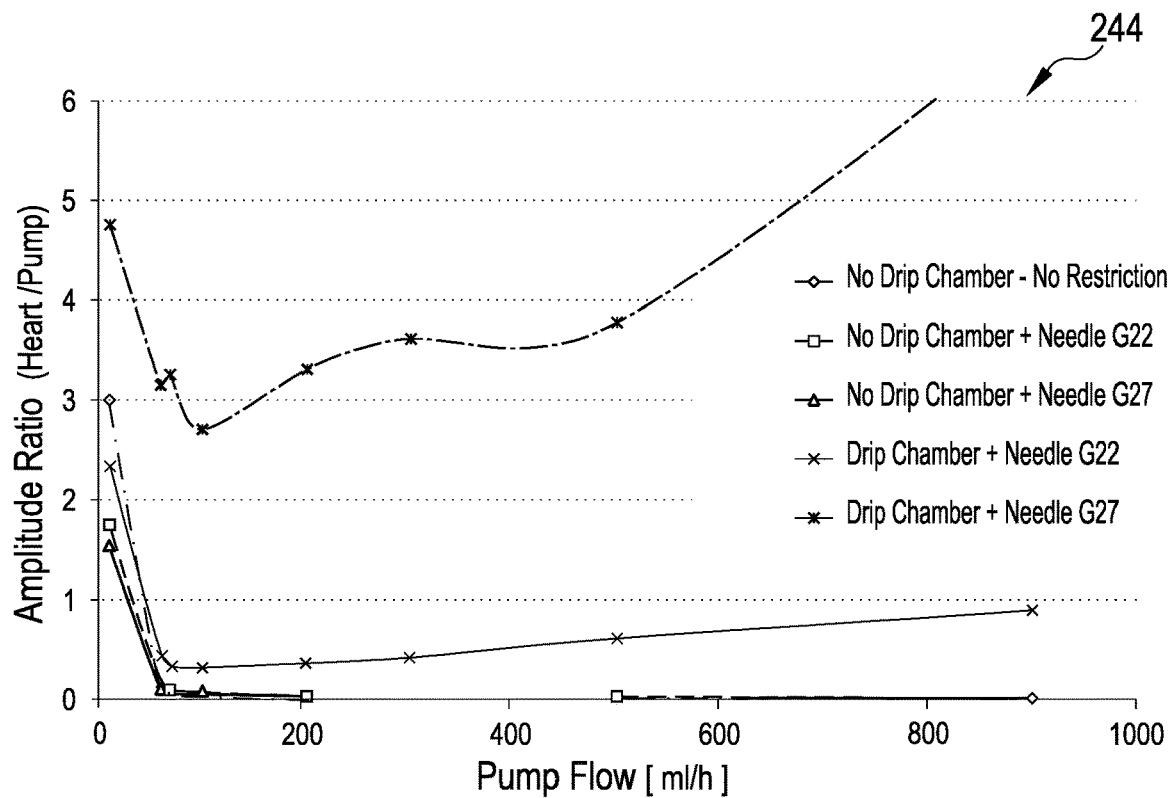
FIG. 4C shows a diagram illustrating pump flow/amplitude ratio occurring in IV infusion sets in accordance with the present invention as compared to an IV infusion set in accordance with prior art designs.

FIG. 4C shows a diagram 244 illustrating pump flow/amplitude ratio occurring in IV infusion sets 10-21 in accordance with the present invention as compared to an IV infusion set 10-10 in accordance with prior art designs. Several graphs show amplitude ratios as measured in IV infusion sets provided with (or without) a compliance element 120 (e.g. a drip chamber) and/or different resistance elements (e.g. 16 to 27 G needle) over pump flow rates (from 0 to 1000 ml/h). The amplitude ratio relates the pressure signals originating from PVP to those of the pump and, thus, a higher ratio is indicative of a stronger PVP signal in relation to the pump signal. In other words, the greater the value of the ratio, the easier it is to determine vital signs from the signal.

As can be seen, a significantly higher ratio can be achieved in IV infusion sets provided with a compliance element 120 (e.g. a drip chamber) and a resistance element 130 (e.g. a G22 or G27 needle). In the example shown, the best (i.e. highest) ratio can be achieved with a combination of a drip chamber and a G27 needle. However, as compared to IV infusion sets lacking a drip chamber, also the combination of a drip chamber and a G22 needle still provides ratios that are significantly higher and, thus, facilitate much more reliable and accurate measurements.

Figure 4D:
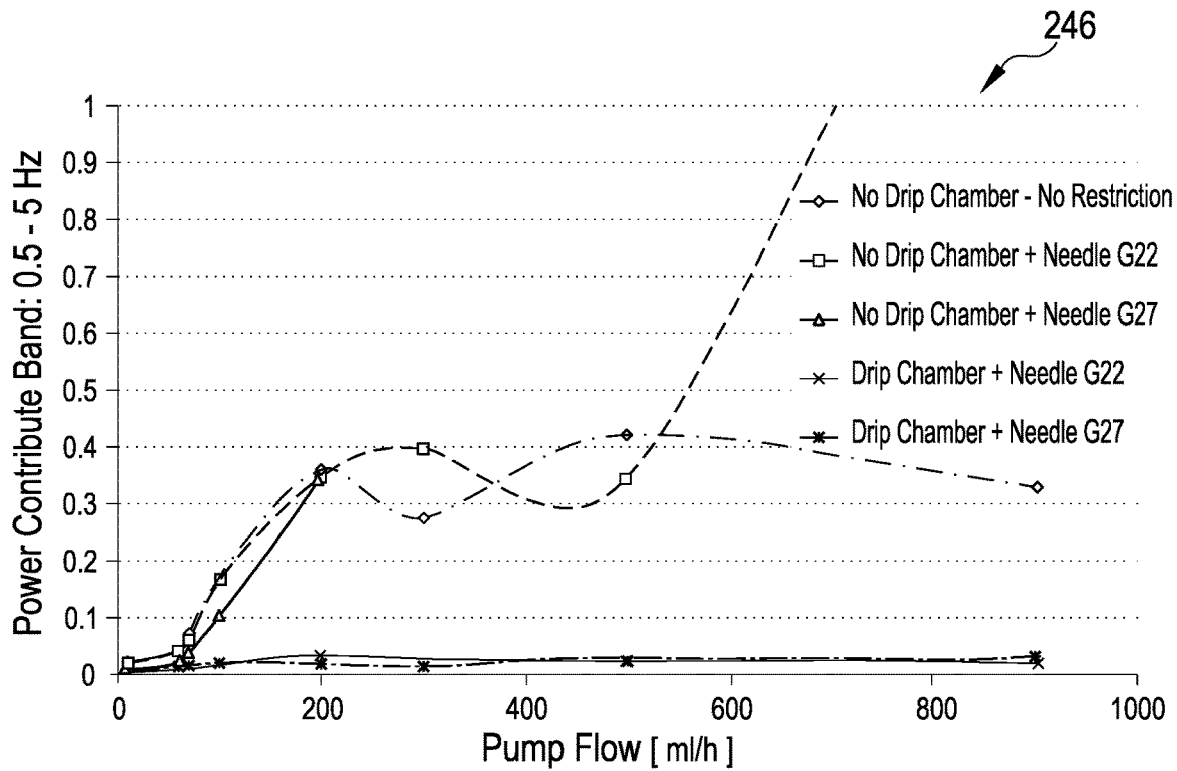
FIG. 4D shows a diagram illustrating pump flow/amplitude ratio occurring in IV infusion sets in accordance with the present invention as compared to an IV infusion set in accordance with prior art designs.

FIG. 4D shows a diagram 246 illustrating pump flow/power contribution occurring in IV infusion sets 10-21 in accordance with the present invention as compared to an IV infusion set 10-10 in accordance with prior art designs. Similar to diagram 244 shown in FIG. 4C, several graphs show power contribution (band: 0.5 Hz to 5 Hz) as measured in IV infusion sets provided with (or without) a compliance element 120 (e.g. a drip chamber) and/or different resistance elements (e.g. 16 to 27 G needle) over pump flow rates (from 0 to 1000 ml/h). The power contribution relates the pressure signals originating from PVP to those of the pump and, thus, a lower contribution is indicative of a stronger PVP signal in relation to the pump signal. In other words, the smaller the value of the contribution within the 0.5 Hz to 5 Hz band, the easier it is to isolate the vital signal.

As can be seen, a significantly lower contribution can be achieved in IV infusion sets provided with a compliance element 120 (e.g. a drip chamber) and a resistance element 130 (e.g. a G22 or G27 needle). In the example shown, the best (i.e. lowest) contribution can be achieved with a combination of a drip chamber and a G27 needle or a G22 needle, thus, facilitating much more reliable and accurate measurements.

Figure 4E:
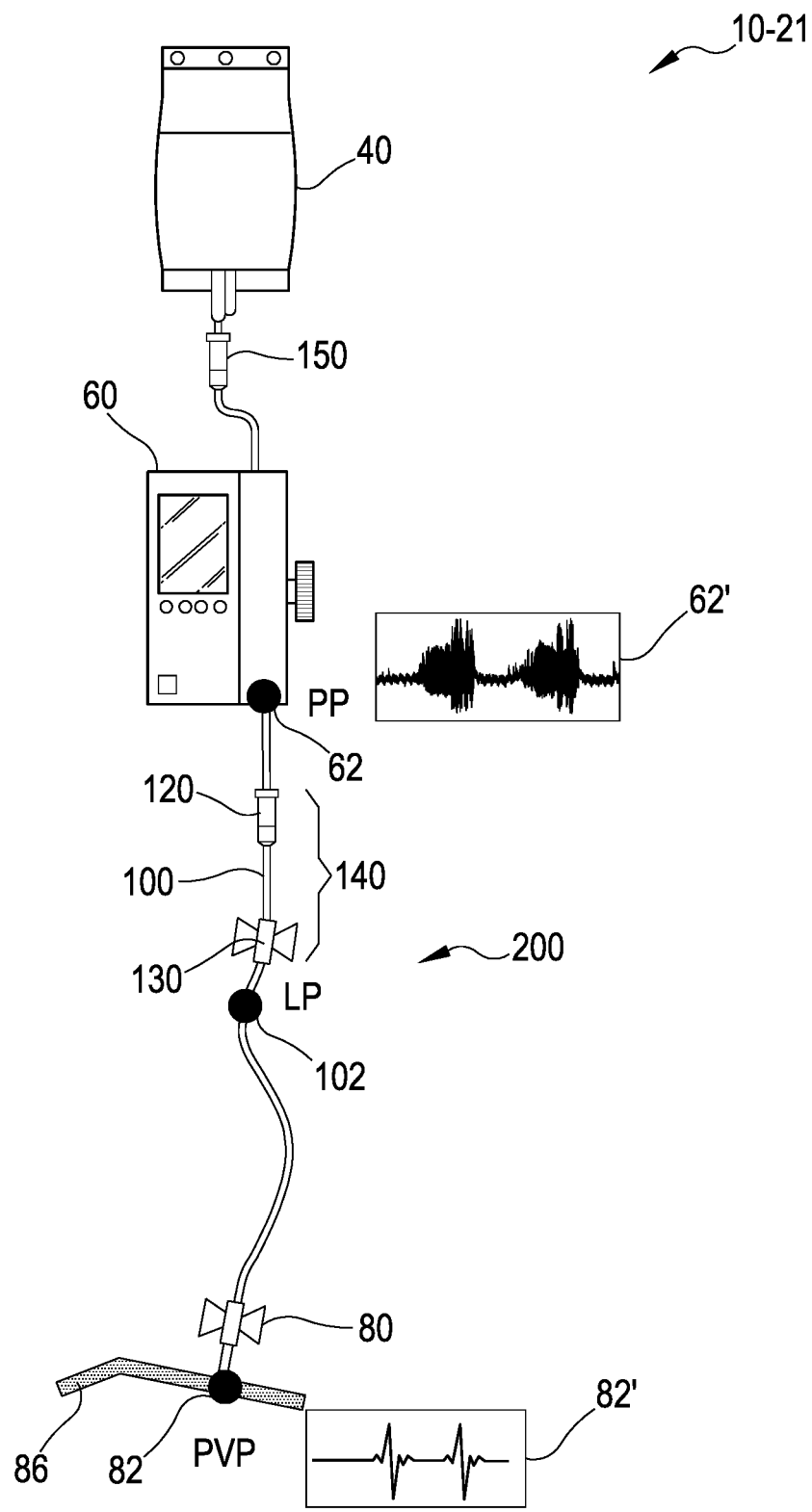
FIG. 4E schematically shows an IV infusion set in accordance with the first embodiment of the present invention FIG. 5 schematically shows an IV infusion set in accordance with a second embodiment of the present invention.

FIG. 4E schematically shows an IV infusion set 10-21 in accordance with the first embodiment of the present invention. The IV infusion set 10-21 includes a source 40 of medical fluid, a drip chamber 150, an infusion apparatus 60 including an infusion pump 62, a compliance element 120 (in the present example also a drip chamber), a resistance element 130, an infusion line 200 including a main infusion line 100, and a patient access 80. The patient access 80 typically comprises a cannula configured to provide access to the cardiovascular system 86 of a patient. The compliance element 120 and the resistance element 130 may be referred to as damping element 140.

The compliance element 120 (e.g. a drip chamber) is located upstream from a position LP at which line pressure LP is to be measured and downstream from pump 62. The resistance element 130 (e.g. a cannula/needle 22 G or 27 G) is located upstream from the position LP at which line pressure LP is to be measured and downstream from compliance element 120. In other words, the damping element 140 combines, in downstream order, compliance element 120 and resistance element 130, and is located upstream from position LP and downstream from pump 62.

During operation of the infusion apparatus 60, medical fluid is supplied from the source 40 medical fluid through main infusion line 100 towards patient access 80, where it is infused into the patient's cardiovascular system 86. The medical fluid is conveyed using a pump 62, for example a peristaltic pump, typically integrated into the infusion apparatus 60. Main infusion line 100 may be provided, for example at position LP, with a pressure sensor 102 configured to detect a pressure of fluid present within main infusion line 100.

Figure 5:
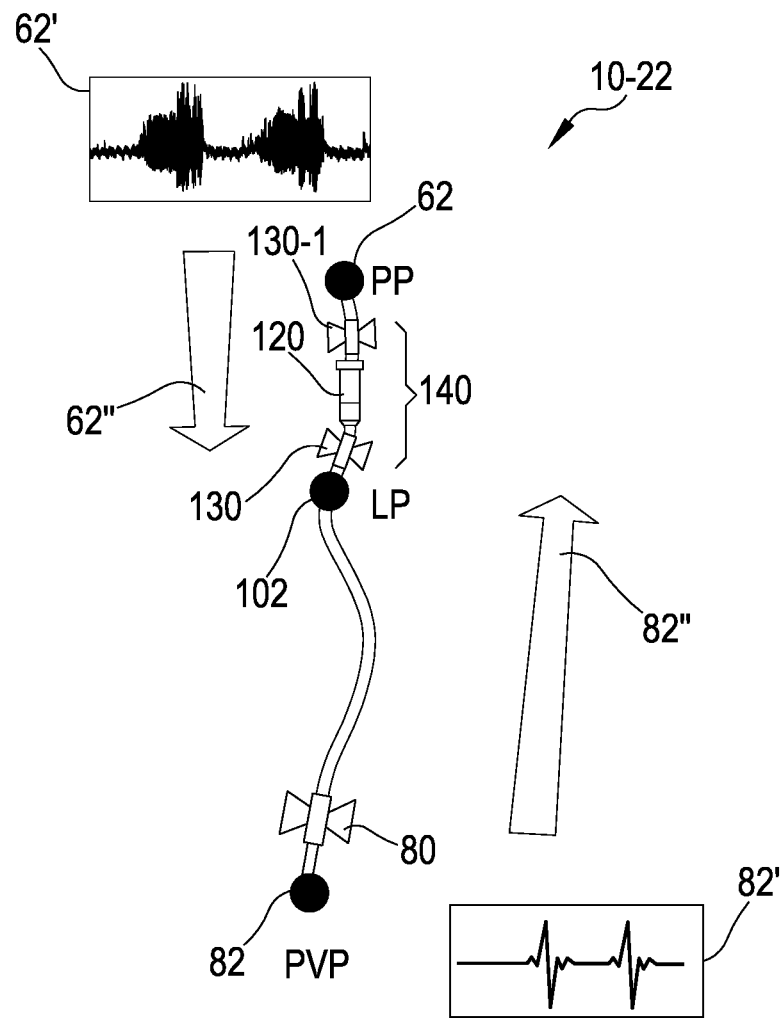
FIG. 5A schematically shows an IV infusion set in accordance with the second embodiment of the present invention.

FIG. 5 schematically shows an IV infusion set 10-22 in accordance with a second embodiment of the present invention. The overall structure of IV infusion set 10-22 is largely identical to that of IV infusion set 10-21 as shown in FIG. 4. However, apart from a compliance element 120 (e.g. a drip chamber) that has been added to main infusion line 100 of IV infusion set 10-22 upstream from a position LP at which line pressure LP is to be measured (or downstream from the pump 62) and a resistance element 130 (e.g. a cannula/needle 22 G or 27 G) that has been added to main infusion line 100 of IV infusion set 10-22 upstream from the position LP at which line pressure LP is to be measured and downstream from compliance element 120, additionally a second resistance element 130-1 (e.g. a cannula/needle 22 G or 27 G) has been added to main infusion line 100 of IV infusion set 10-22 upstream from the compliance element 120 and downstream from infusion apparatus 60 (i.e. downstream from the pump 62). The compliance element 120 and the resistance elements 130 and 130-1 may be referred to as damping element 140. In such terms, the damping element 140 of IV infusion set 10-22 combines, in downstream order, second resistance element 130-1, compliance element 120, and resistance element 130, and is located upstream from position LP and downstream from pump 62.

As described above, and also in the IV infusion set 10-22, pressure waves lose energy while propagating along main infusion line 100 as described above with respect to FIG. 4. This is also illustrated in FIG. 5 by arrows 62" and 82".

The compliance element 120 arranged upstream position LP dampens or attenuates the pressure propagating along main infusion line 100 as described above with respect to FIG. 4. Also, resistance element 130 reflects pressure propagating along main infusion line 100, thus effectively acting as an amplifier of such pressure as described above with respect to FIG. 4. Additionally, the second resistance element 130-1 reflects pump pressure propagating downstream along main infusion line 100 and reflecting PVP propagating upstream along main infusion line 100. Therefore, the combination of compliance element 120, resistance element 130, and second resistance element 130-1 serves to further reduce unwanted pump signal spectrum component and to further amplify PVP with respect to position LP.

Figure 5A:
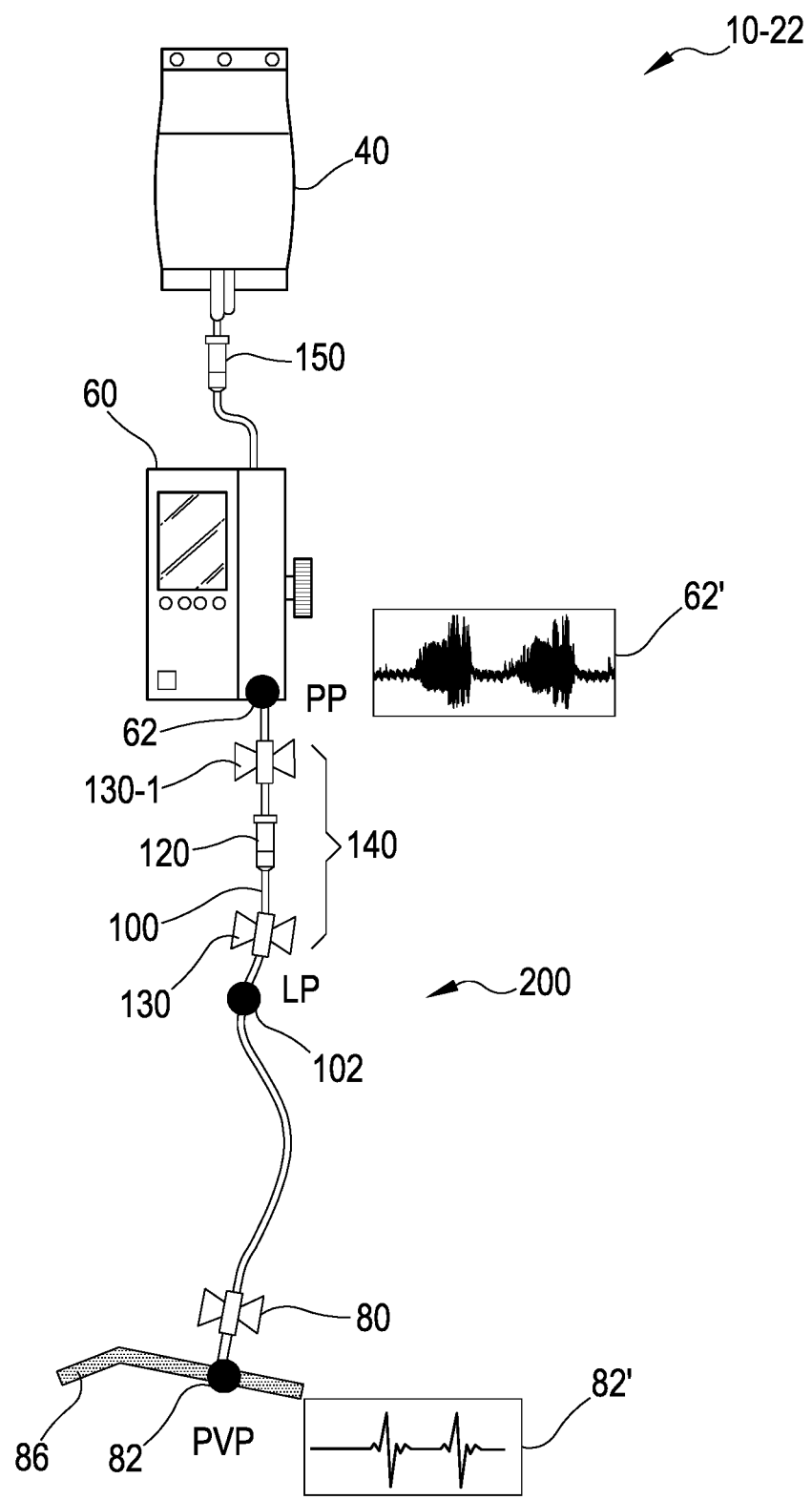

FIG. 5A schematically shows an IV infusion set 10-22 in accordance with the second embodiment of the present invention. The IV infusion set 10-22 includes a source 40 of medical fluid, a drip chamber 150, an infusion apparatus 60 including an infusion pump 62, a second resistance element 130-1, a compliance element 120 (in the present example a drip chamber), a resistance element 130, an infusion line 200 including a main infusion line 100, and a patient access 80. The patient access 80 typically comprises a cannula configured to provide access to the cardiovascular system 86 of a patient. The second resistance element 130-1, the compliance element 120, and the resistance element 130 may be referred to as damping element 140.

The compliance element 120 (e.g. a drip chamber) is located upstream from a position LP at which line pressure LP is to be measured and downstream from pump 62. The resistance element 130 (e.g. a cannula/needle 22 G or 27 G) is located upstream from the position LP at which line pressure LP is to be measured and downstream from compliance element 120. The second resistance element 130-1 (e.g. a cannula/needle 22 G or 27 G) is located upstream from the compliance element 120 and downstream from infusion apparatus 60 (i.e. downstream from the pump 62).

During operation of the infusion apparatus 60, medical fluid is supplied from the source 40 medical fluid through main infusion line 100 towards patient access 80, where it is infused into the patient's cardiovascular system 86. The medical fluid is conveyed using a pump 62, for example a peristaltic pump, typically integrated into the infusion apparatus 60. Main infusion line 100 may be provided, for example at position LP, with a pressure sensor 102 configured to detect a pressure of fluid present within main infusion line 100.

Figure 6:
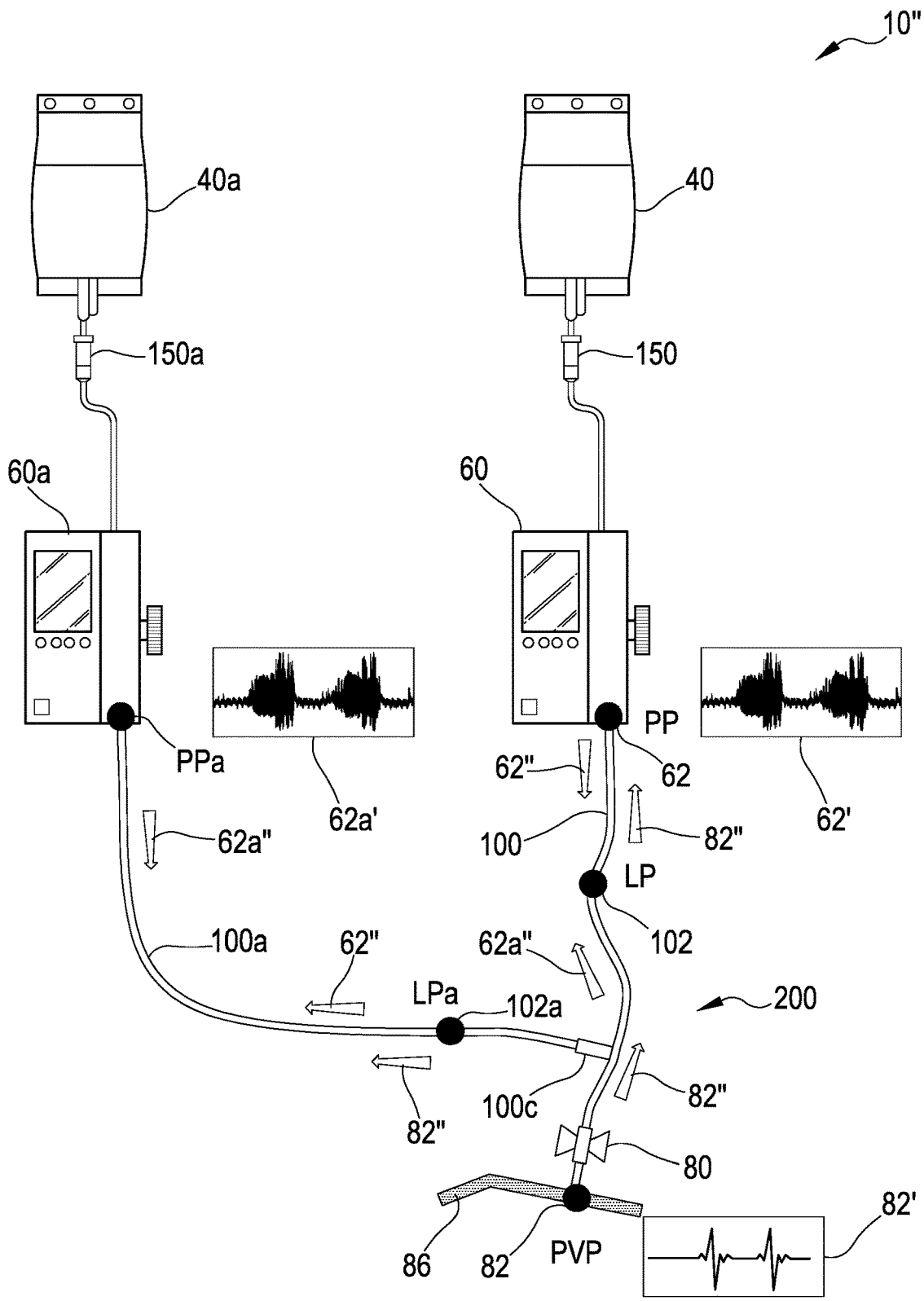
FIG. 6 schematically shows a third known IV infusion set having a main infusion line and an auxiliary infusion line.

FIG. 6 schematically shows a third known IV infusion set 10" having an infusion line 200 including both a main infusion line 100 and an auxiliary infusion line 100a. The IV infusion set 10" includes, on a main infusion line 100, a source 40 of medical fluid, a drip chamber 150, an infusion apparatus 60 including an infusion pump 62, and a patient access 80. The patient access 80 typically comprises a cannula configured to provide access to the cardiovascular system 86 of a patient. The IV infusion set 10" further includes, on an auxiliary infusion line 100a, an auxiliary source 40a of medical fluid, an auxiliary drip chamber 150a, and an auxiliary infusion apparatus 60a including an auxiliary infusion pump 62a. The auxiliary infusion line 100a is connected to the main infusion line 100 by an infusion line connector 100c (e.g. a Luer connector), the connection being realized along the main infusion line 100 between the patient access 80 and the infusion pump 62, typically proximate the patient access 80.

During operation of infusion apparatuses 60 and/or 60a, medical fluid is supplied from one or both of sources 40 and 40a of medical fluid through main infusion line 100 and/or auxiliary infusion line 100a towards patient access 80, where it is infused into the patient's cardiovascular system 86. The medical fluid is conveyed using pumps 62 and/or 62a (e.g. either or both including a peristaltic pump), typically integrated into the infusion apparatuses 60 and/or 60a. Similar to main infusion line 100, auxiliary infusion line 100a may be provided, for example at position LPa, with a pressure sensor 102a configured to detect a pressure of fluid present within auxiliary infusion line 100a.

FIG. 6 further illustrates effects that typically occur during operation of the IV infusion set 10". Diagrams 62' and 62a' illustrate corresponding pressure signals typically observable downstream from the respective pumps 62 and 62a, for example at positions PP and PPa on infusion lines 100 and 100a. Pressure signals as shown in diagrams 62' and 62a' may contain unwanted pump signal spectrum components as described above. At position PP, a pressure signal taken from a pressure sensor may generally correspond to the signal illustrated in diagram 62'. The pressure signal shown in diagram 62' is indicative of the pressure in main infusion line 100 at position PP and may suffer from disturbances caused by operation of the pump 62 upstream from or approximately at position PP. Similarly, at position PPa, a pressure signal taken from a pressure sensor may generally correspond to the signal illustrated in diagram 62a'. The pressure signal shown in diagram 62a' is indicative of the pressure in auxiliary infusion line 100a at position PPa and may similarly suffer from disturbances caused by operation of the pump 62a upstream from or approximately at position PPa.

With respect to the IV infusion set 10", a combination of several unwanted pump signal spectrum components may be generated during infusion and may propagate through the IV infusion set 10" in several ways. As described above, pump signal spectrum components typically lose energy while propagating along infusion lines 100 and 100a. This is illustrated in FIG. 6 by arrows 62" and 62a". PVP pressure signals 82" also propagate through the infusion lines 100 and 100a. Pump signal spectrum components caused by pump 62, for example, travel downstream along main infusion line 100, i.e. in direction 62". It is noted that the pump signal spectrum components originating at pump 62 propagate not only downstream along main infusion line 100, but also upstream auxiliary infusion line 100a, from connector 100c, which is configured to put infusion lines 100 and 100a into fluid communication with one another. Again, the amplitude of these pump signal spectrum components decreases in direction 62" along both infusion lines 100 and 100a, inter alia depending upon attenuation properties of infusion lines 100 and 100a, and further depending upon the specific connection realized by connector 100c.

Similarly, pump signal spectrum components caused by pump 62a, for example, travel downstream along auxiliary infusion line 100a, i.e. in direction 62a", and, similar to what is described above with respect to pump 62, not only downstream along auxiliary infusion line 100a, but also upstream main infusion line 100, from connector 100c, which is configured to put infusion lines 100 and 100a into fluid communication with one another. Again, the amplitude of these pump signal spectrum components decreases in direction 62a" along both infusion lines 100a and 100, inter alia depending upon attenuation properties of infusion lines 100a and 100, and further depending upon the specific connection realized by connector 100c.

Similarly, PVP waves originating from the cardiovascular system of a patient, travel upstream along infusion lines 100 and 100a, i.e. in direction 82", and the amplitude of these pressure waves decreases along infusion lines 100 and 100a in a manner similar to what is described above with respect to the pump signal spectrum components originating at pumps 62 and 62a. When using an auxiliary infusion line 100a, the amplitude of PVP waves not only decreases along main infusion line 100 and along auxiliary infusion line 100a, but is also attenuated due to the fact that the PVP waves originating in the vascular system of the patient will be divided between main infusion line 100 and auxiliary infusion line 100a going upstream from the connector 100c. The PVP waves propagating along auxiliary infusion line 100a only include a portion of the original heart contribute (e.g. signal power or amplitude) and the PVP waves propagating along main infusion line 100 only include a remaining portion of the original heart contribute. The magnitude of the PVP waves upstream from connector 100c is, thus, smaller in main infusion line 100 and in auxiliary infusion line 100a than downstream from connector 100c (where the PVP waves originate).

Again, an example signal indicative of the PVP is illustrated in diagram 82'. As described above with respect to figure I.A, it is desired to measure the PVP within the main infusion line 100, for example at position LP, or within the auxiliary infusion line 100a, for example at position LPa. However, the effective pressure signal that can be obtained at positions LP and/or LPa is typically affected both by disturbances caused by the pumps 62 and/or 62a (as shown in diagrams 62' and 62a') and propagating from positions PP and/or PPa, respectively, towards positions LP and/or LPa, respectively, as well as by the actual PVP signal present within the cardiovascular system 86 of a patient and propagating upstream from the patient access 80 towards positions LP and LPa.

Figure 6A:
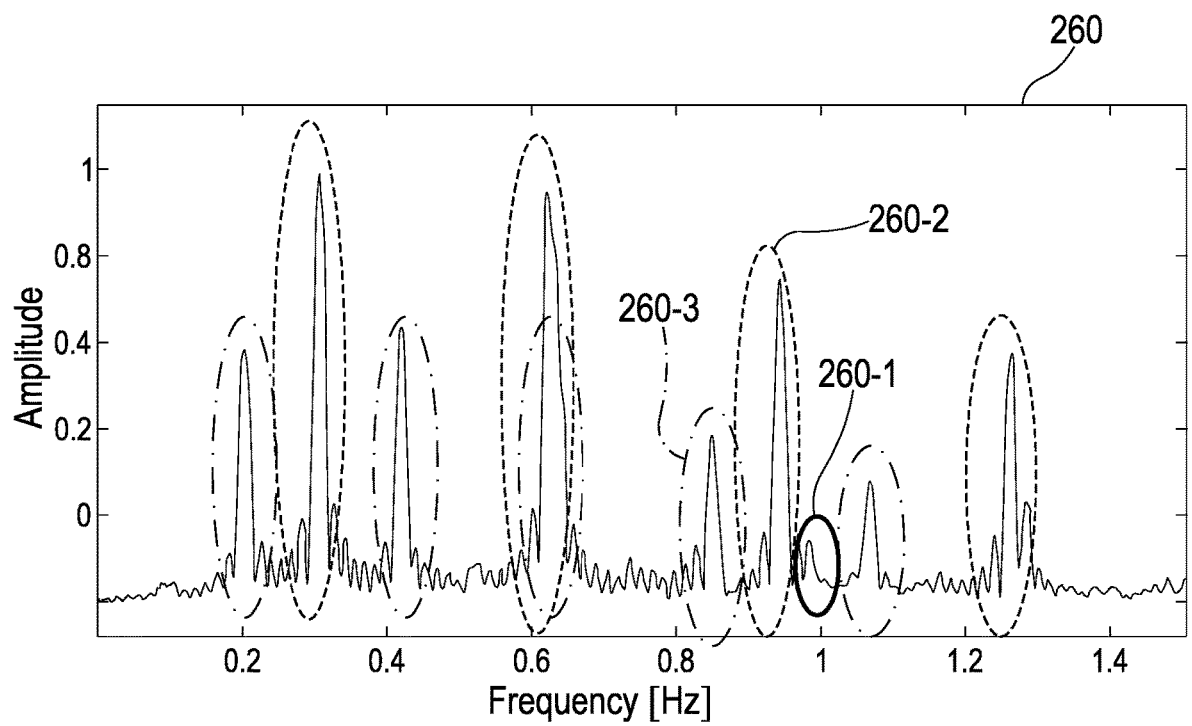
FIG. 6A shows a diagram illustrating frequency/amplitude for signals measured in the third known IV infusion set of FIG. 6.

FIG. 6A shows a diagram 260 illustrating frequency/amplitude for signals measured in the third known IV infusion set 10" of FIG. 6. The example data shown in diagram 260 was collected based on an IV infusion set in which the pump 62 was operated at about 100 ml/h, auxiliary pump 62a was operated at about 70 ml/h, the PVP had a pressure of about 2 mmHg at 1 Hz (60 beats per minute), the patient access 80 included a 20 G needle/cannula and the fluid used was water. As can be seen from the frequency spectrum shown in diagram 260, the heart contribute 260-1 exhibits a rather small FFT amplitude in comparison to the pump 62 contribute 260-2 and the auxiliary pump 62a contribute 260-3. Under some conditions, for example at different flow rates of the pumps 62 and/or 62a, the corresponding contributes 260-2 and 260-3 may substantially overlap the frequency of the heart contribute 260-1 and, thus, make detection thereof more difficult or impossible.

Figure 6B:
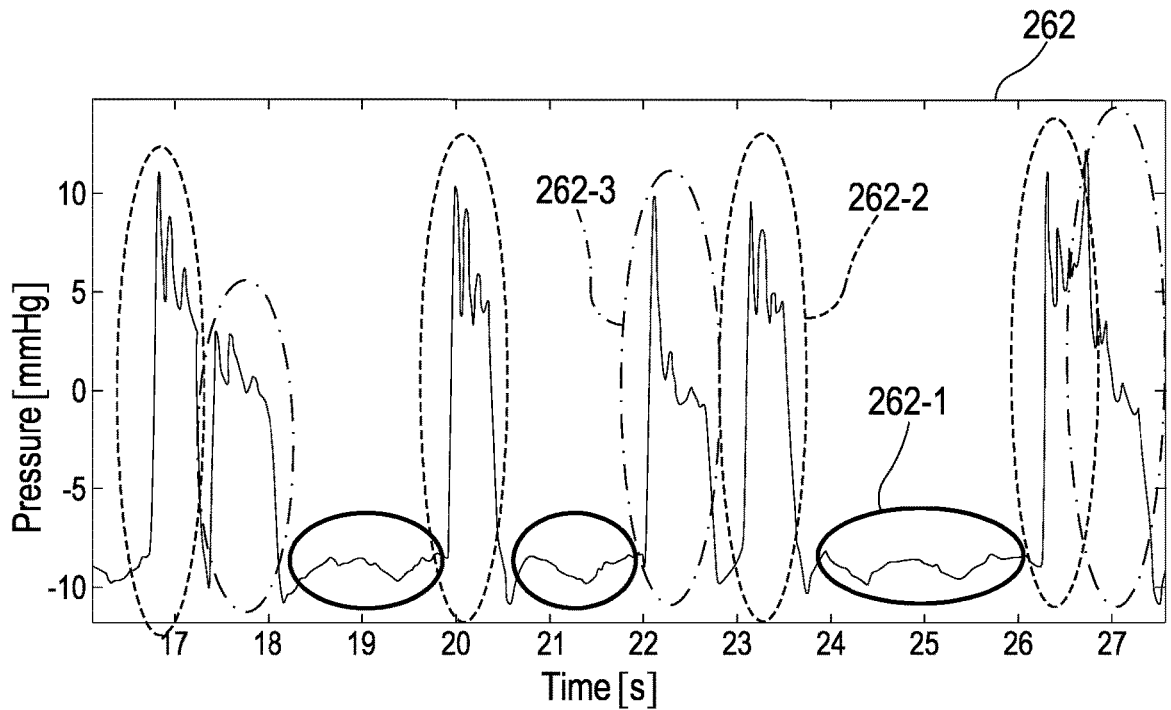
FIG. 6B shows a diagram illustrating pressure/time for signals measured in the third known IV infusion set of FIG. 6.

FIG. 6B shows a diagram 262 illustrating pressure/time for signals measured in the third known IV infusion set 10" of FIG. 6. The example data shown in diagram 260 was collected under the same conditions as described above with respect to FIG. 6A. As can be seen from the time spectrum shown in diagram 262, the heart contribute 262-1, again, exhibits a rather small pressure amplitude in comparison to the pump 62 contribute 262-2 and the auxiliary pump 62a contribute 262-3, both of which register at several magnitudes higher. As can be seen from diagram 262, the pump contributes 262-2 and 262-3 substantially overlap the amplitudes of the heart contribute 260-1 during several time intervals (see, e.g., between 17 and 18 seconds, and around 20 seconds), thus making detection of the heart contribute 260-1 more difficult or impossible during such time intervals.

Figure 7:
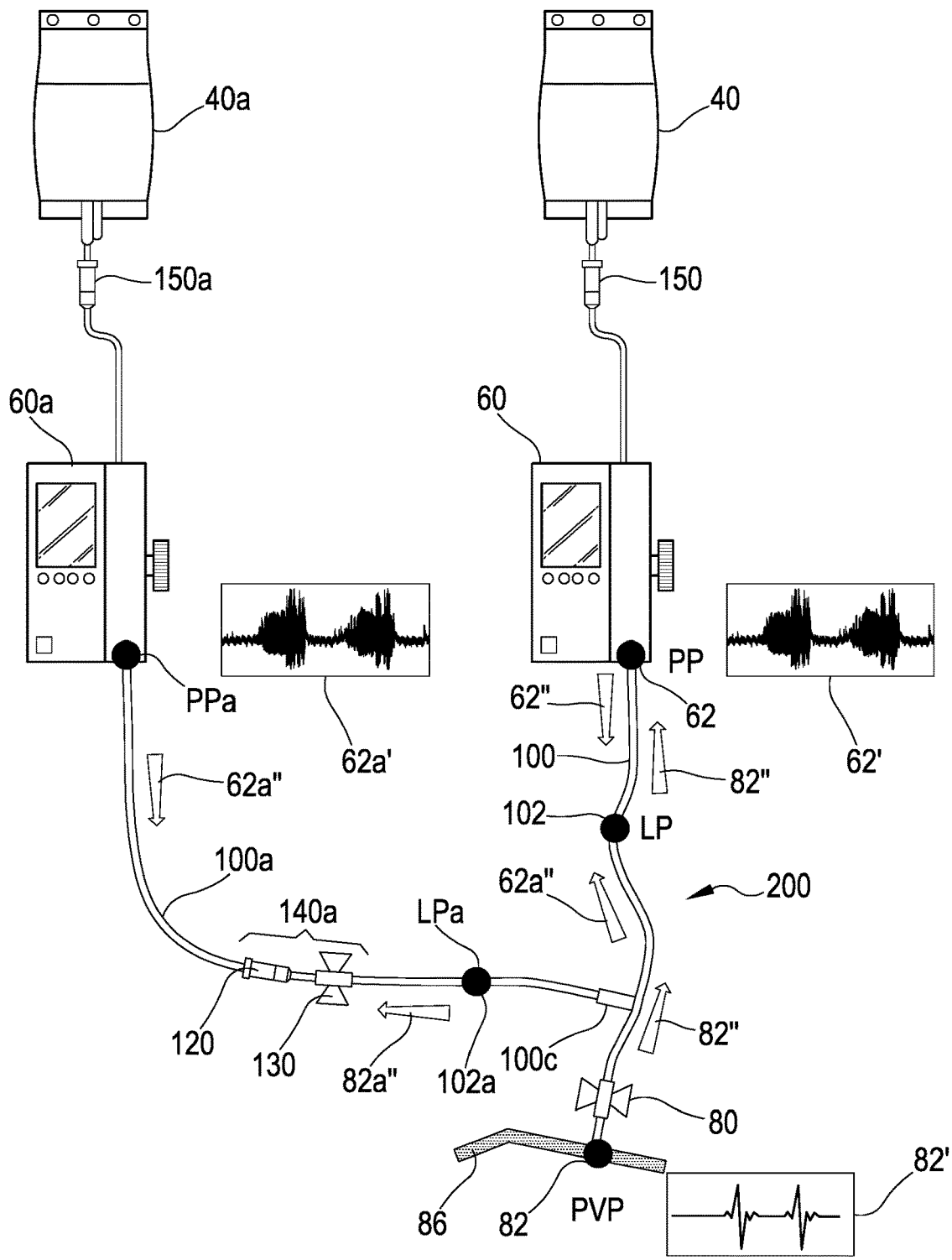
FIG. 7 schematically shows an IV infusion set in accordance with a third embodiment of the present invention.

FIG. 7 schematically shows an IV infusion set 10-23 in accordance with a third embodiment of the present invention. The IV infusion set 10-23 is structurally similar to the IV infusion set 10" as shown in FIG. 6, except for a damping element 140a arranged on the auxiliary infusion line 100a. Reference numerals identical in FIGS. 7 and 6, thus, refer to corresponding elements. It is noted that the embodiment in FIG. 7 illustrates an example in which infusion line 200 includes a main infusion line 100 and a (single) auxiliary infusion line 100a. However, in some examples the IV infusion set 10-23 may comprise an infusion line 200 including a main infusion line 100 and two (or more) auxiliary infusion lines 100a. What is described below with respect to a single auxiliary infusion line 100a is, thus, also applicable to multiple auxiliary infusion lines 100a.

As already described above, damping element 140a in FIG. 7 may include one or more compliance 120 and resistance 130, 130-1 elements. The example illustrated in FIG. 7 shows damping element 140a including a compliance element 120 and a resistance element 130 (as described above, e.g., with respect to FIGS. 4 and 4E). For reasons of clarity, not all possible combinations of compliance and resistance elements are shown in FIG. 7. It is understood, however, that auxiliary infusion line 100a may include, for example, a compliance element 120 and a resistance element 130 as shown (as described above and as also shown, e.g., in FIGS. 4 and 4E), or a compliance element 120 and resistance elements 130, 130-1 (as described above and as shown, e.g., in FIGS. 5 and 5A).

It is noted that damping element 140a may be arranged on auxiliary infusion line 100a as shown in FIG. 7 (e.g. somewhere along line 100a), or it can be realized as an accessory device directly attached to or integral with connector 100c. In some embodiments, connector 100c includes damping element 140a. In other embodiments, damping element 140a includes connector 100c. In such examples, the position LPa is adjusted accordingly with the position of damping element 140a.

The respective arrangement of the respective components of damping element 140a corresponds to what is described above and to what is shown in FIGS. 4, 4E, 5, and 5A. In one example of an IV infusion set 10-23 in accordance with the third embodiment and having a damping element 140a corresponding to damping element 140 shown in FIGS. 4 and 4E, a compliance element 120 (e.g. a drip chamber) is located on auxiliary infusion line 100a upstream from position LPa at which line pressure LPa is to be measured and downstream from pump 62a. A resistance element 130 (e.g. a cannula/needle 16 G to 27 G) is located upstream from the position LPa at which line pressure LPa is to be measured and downstream from compliance element 120.

In another example of an IV infusion set 10-23 in accordance with the third embodiment and having a damping element 140a corresponding to damping element 140 shown in FIGS. 5 and 5A, the auxiliary infusion line 100a includes elements 120 and 130 as described with respect to the previous example as shown on FIG. 7. Additionally, auxiliary infusion line 100a includes a second resistance element 130-1 (e.g. a cannula/needle 16 G to 27 G; not shown separately in FIG. 7) located upstream from the compliance element 120 and downstream from infusion apparatus 60a (i.e. downstream from pump 62a).

During operation of the infusion apparatuses 60 and 60a, medical fluid is supplied from the sources 40 and 40a of medical fluid through infusion lines 100 and 100a towards patient access 80, where it is infused into the patient's cardiovascular system 86. The medical fluid is conveyed using pumps 62 and 62a.

Generally, pump signal spectrum components originating at pumps 62 and 62a, as well as PVP waves propagate through infusion lines 100 and 100a as described above with respect to FIG. 6. However, due to the effects of the damping element 140a arranged on auxiliary infusion line, unwanted pump signal spectrum components originating at auxiliary infusion pump 62a are attenuated such that they do not, or to a much lesser degree, propagate into and along main infusion line 100. To this aim, damping element 140a may include a compliance element 120 configured to attenuate pump signal spectrum components at frequencies in a range of 0.67 Hz or higher. Further, due to the effects of the damping element 140a arranged on auxiliary infusion line, the PVP signal is restricted from propagating along auxiliary infusion line 100a upstream from damping element 140a and, thus, is not substantially, or to a much lesser degree, drained. To this aim, damping element 140a may include one or more resistance elements 130 and 130-1 configured to restrict fluid flow through auxiliary infusion line 100a.

Figure 7A:
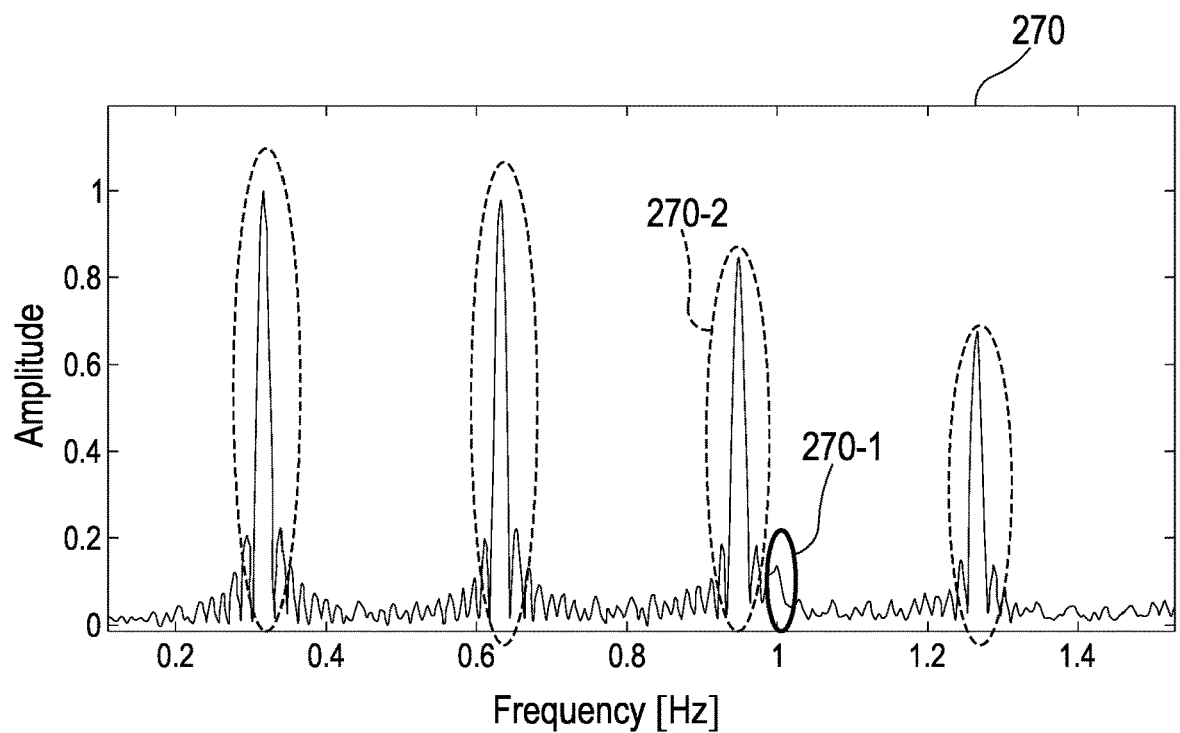
FIG. 7A shows a diagram illustrating frequency/amplitude for example signals measured in the IV infusion set in accordance with the third embodiment of the present invention.

FIG. 7A shows a diagram 270 illustrating frequency/amplitude for example signals measured in the IV infusion set 10-23 in accordance with the third embodiment of the present invention. The example data shown in diagram 270 was collected under the same conditions as described above with respect to FIG. 6A. As can be seen from the frequency spectrum shown in diagram 270, the heart contribute 270-1 exhibits a rather small FFT amplitude in comparison to the pump 62 contribute 270-2. However, in contrast to what is shown in diagram 260 of FIG. 6A, the auxiliary pump 62a contribute (shown as 260-3 in FIG. 6A) is absent from the spectrum. Therefore, the unwanted pump signal spectrum components originating at auxiliary infusion pump 62a are attenuated by damping element 140a (as described above with respect to FIG. 7) such that they are substantially absent from the frequency spectrum and practically do not propagate into and along main infusion line 100. This significantly improves the possibilities for obtaining a clean signal indicative of the heart contribute 270-1.

Figure 7B:
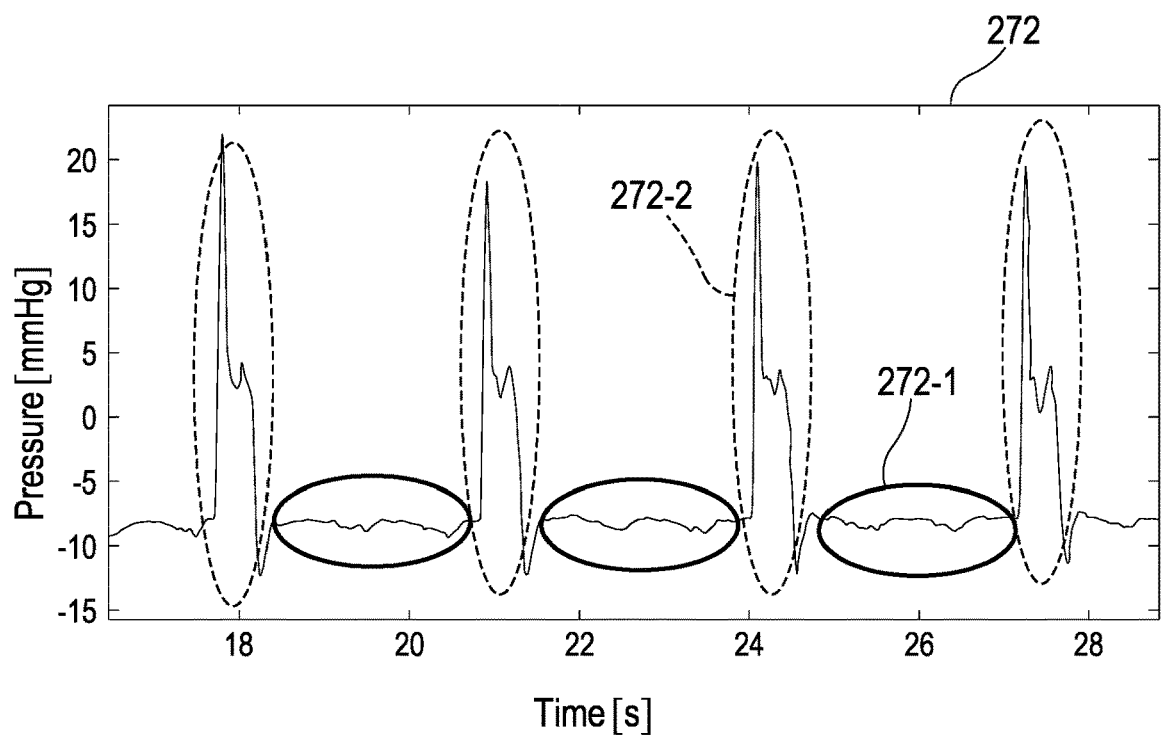
FIG. 7B shows a diagram illustrating pressure/time for example signals measured in the IV infusion set in accordance with the third embodiment of the present invention.

FIG. 7B shows a diagram illustrating pressure/time for example signals measured in the IV infusion set 10-23 in accordance with the third embodiment of the present invention. The example data shown in diagram 272 was collected under the same conditions as described above with respect to FIG. 7A. As can be seen from the time spectrum shown in diagram 272, the heart contribute 272-1, again, exhibits a rather small pressure amplitude in comparison to the pump 62 contribute 272-2. However, the auxiliary pump 62a contribute is substantially absent from diagram 272.

The damping element 140a, thus, can advantageously reduce or eliminate unwanted pump signal spectrum components originating at auxiliary infusion pump 62a, thereby improving the detection of a signal indicative of the heart contribute 272-1.

Figure 8:
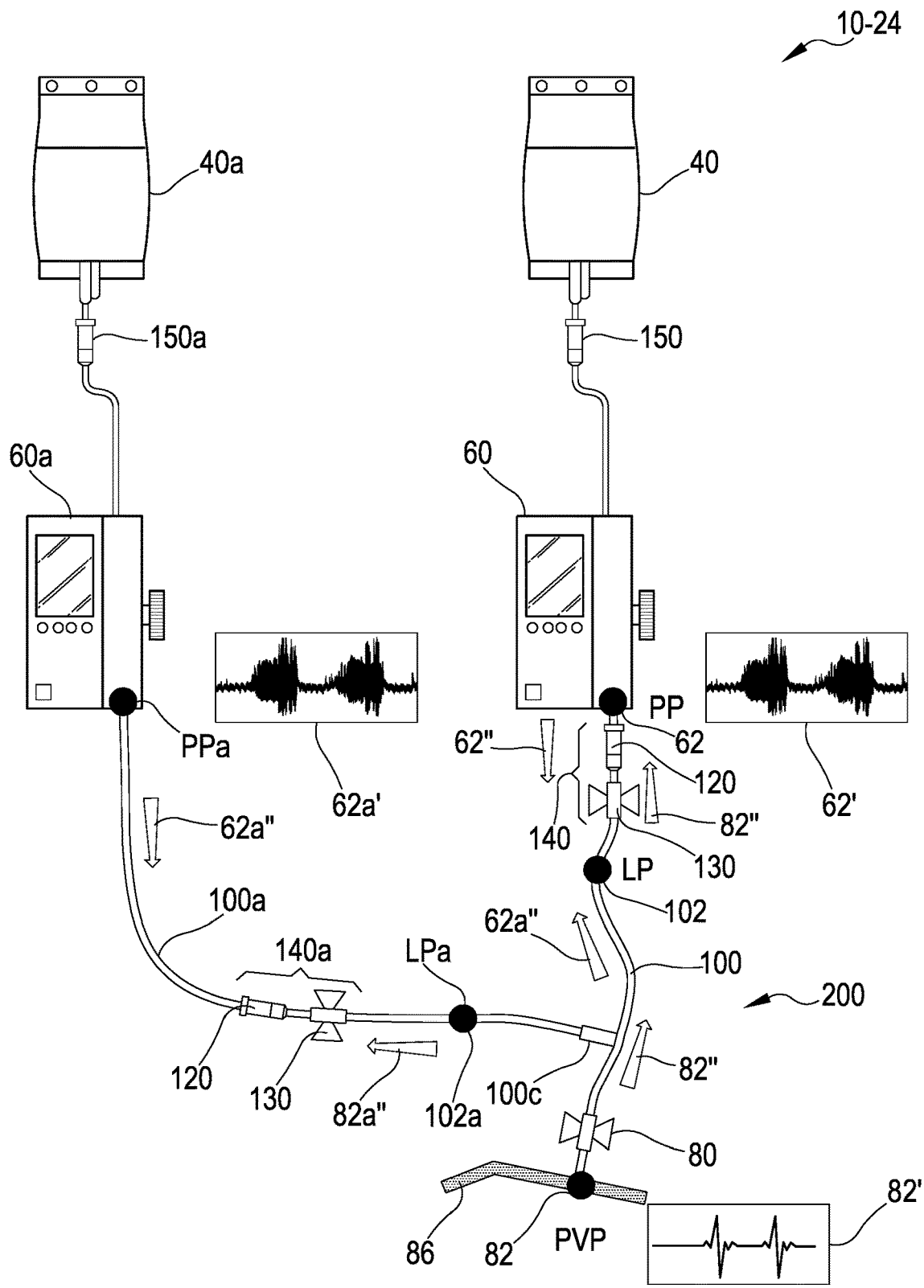
FIG. 8 schematically shows an IV infusion set in accordance with a fourth embodiment of the present invention.

FIG. 8 schematically shows an IV infusion set 10-24 in accordance with a fourth embodiment of the present invention. The IV infusion set 10-24 is structurally similar to the IV infusion set 10-23 as shown in FIG. 7, except for an additional damping element 140 arranged on the main infusion line 100. Reference numerals identical in FIGS. 8 and 7, thus, refer to corresponding elements.

As already described above and similar to damping element 140a as shown in FIG. 7, damping element 140 in FIG. 8 may also include one or more compliance 120 and resistance 130, 130-1 elements. For reasons of clarity, not all combinations of compliance and resistance elements are shown in FIG. 8. It is understood, however, that main infusion line 100 may include, for example, a compliance element 120 and a resistance element 130 as shown (and as described above and as also shown, e.g., in FIGS. 4 and 4E), or a compliance element 120 and resistance elements 130, 130-1 (as described above and as shown, e.g., in FIGS. 5 and 5A). There is no limitation or restriction as to the combination of compliance and/or resistance elements, when several damping elements 140, 140a are present. For example, damping elements 140 and 140a may have the same structure (e.g. both having a compliance element 120 and a resistance element 130), or a different structure (e.g. having a different number of resistance elements).

It is noted that damping element 140 may be arranged on main infusion line 100 as shown in FIG. 8 (e.g. somewhere along main infusion line 100), or it can be realized as an accessory device directly attached to or integral with connector 100c or a corresponding receiving connector or port for connector 100c. In some embodiments, damping element 140 may include a port configured to receive connector 100c. In other examples, an integrated damping element may include damping elements 140 and 140a. In such embodiments, the integrated damping element may also be configured to fluidly connect auxiliary infusion line 100a and main infusion line 100, eliminating the need for connector 100c. The position of LP and/or LPa may be adjusted accordingly in such examples.

The respective arrangement of the respective components of damping element 140 corresponds to what is described above and to what is shown in FIGS. 4, 4E, 5, and 5A. In one example of an IV infusion set 10-24 in accordance with the fourth embodiment and having damping elements 140 and 140a corresponding to damping element 140 shown in FIGS. 4 and 4E, a compliance element 120 (e.g. a drip chamber) is located on auxiliary infusion line 100a upstream from position LPa at which line pressure LPa is to be measured and downstream from pump 62a, and a compliance element 120 (e.g. a drip chamber) is located on main infusion line 100 upstream from position LP at which line pressure LP is to be measured and downstream from pump 62. A resistance element 130 (e.g. a cannula/needle 16 G to 27 G) is located on auxiliary infusion line 100a upstream from position LPa at which line pressure LPa is to be measured and downstream from compliance element 120, and a resistance element 130 (e.g. a cannula/needle 16 G to 27 G) is located on main infusion line 100 upstream from position LP at which line pressure LP is to be measured and downstream from compliance element 120.

Other examples of an IV infusion set 10-24 in accordance with the fourth embodiment and having damping elements 140 and 140a may include one or more damping elements corresponding to damping element 140 shown in FIGS. 5 and 5A and/or one or more damping elements corresponding to damping element 140 shown in FIGS. 4 and 4E.

During operation of the infusion apparatuses 60 and/or 60a, medical fluid is supplied from the sources 40 and 40a medical fluid through infusion lines 100 and 100a towards patient access 80, where it is infused into the patient's cardiovascular system 86. The medical fluid is conveyed using pumps 62 and 62a.

Generally, pump signal spectrum components originating at pumps 62 and 62a, as well as PVP waves propagate through infusion lines 100 and 100a as described above with respect to FIG. 6. However, due to the effects of the damping element 140a arranged on auxiliary infusion line, unwanted pump signal spectrum components originating at auxiliary infusion pump 62a are attenuated such that they do not, or to a much lesser degree, propagate into and along main infusion line 100. To this aim, damping element 140a may include a compliance element 120 configured to attenuate pump signal spectrum components at frequencies in a range of 0.67 Hz or higher. Further, due to the effects of the damping element 140a arranged on auxiliary infusion line, the PVP signal is restricted from propagating along auxiliary infusion line 100a upstream from damping element 140a and, thus, is not substantially, or to a much lesser degree, drained. To this aim, damping element 140a may include one or more resistance elements 130 and 130-1 configured to restrict fluid flow through auxiliary infusion line 100a.

Figure 9:
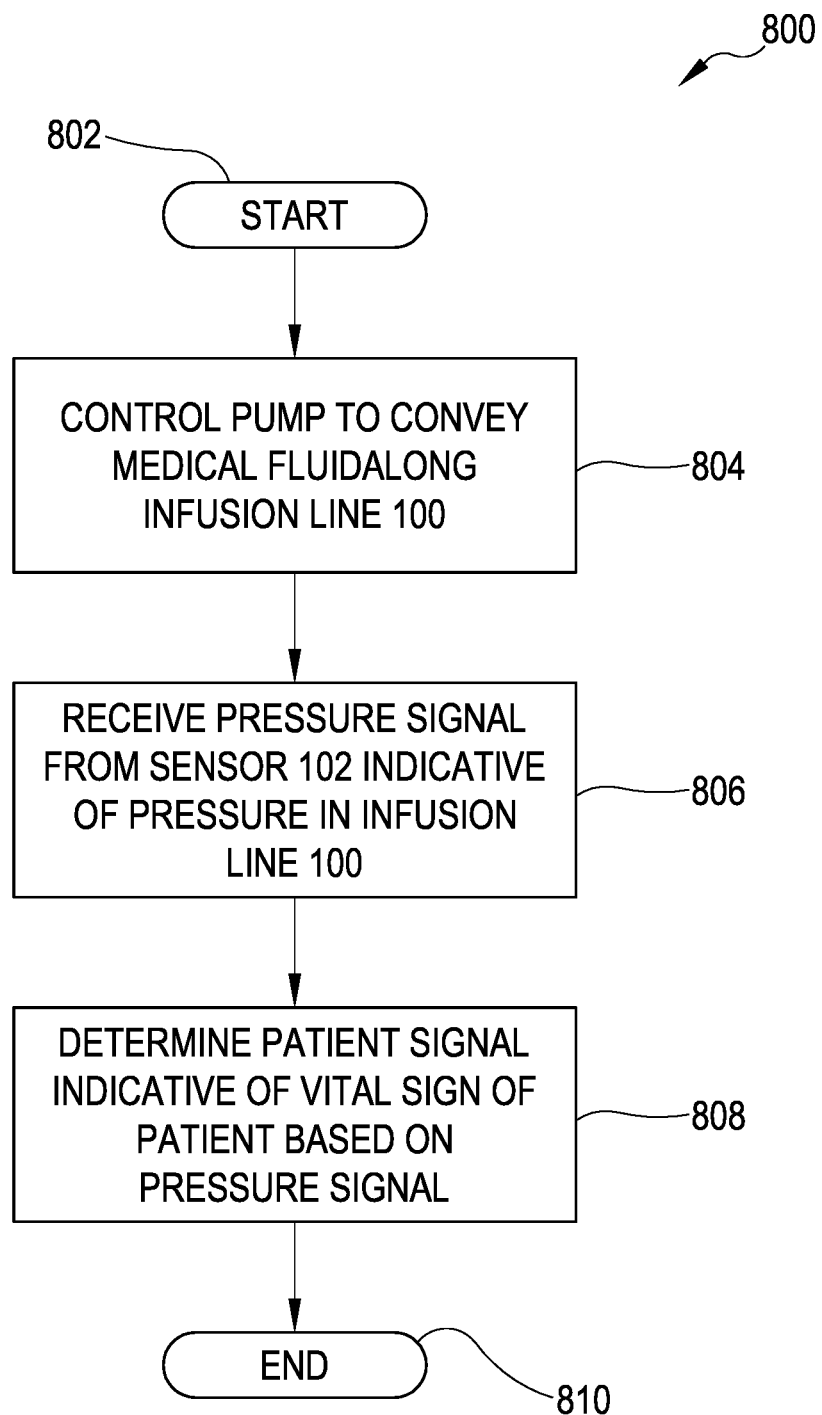
FIG. 9 illustrates a process for determining vital signs of a patient in accordance with the present invention.

FIG. 9 illustrates a process 800 for determining vital signs of a patient in accordance with the present invention. At step 802, process 800 starts. In step 804, the control unit controls pump 62 to convey medical fluid along main infusion line 100. In step 806, the control unit receives a pressure signal from sensor 102, the pressure signal being indicative of a pressure in main infusion line 100. In step 808, the control determines a patient signal indicative of vital sign of patient based on the pressure signal. Process 800 ends at step 810.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. An IV infusion set, comprising:
a patient access configured to connect to a vascular system of a patient;
a source of a medical fluid;
an infusion line having at least one first end configured to connect to the medical fluid source and at least one opposite second end configured to deliver the medical fluid towards the patient access, the infusion line defining at least a medical fluid path developing from the first end of the infusion line to the patient access, the second end of the infusion line being connected to the patient access, the medical fluid source being coupled to the first end of the infusion line and configured to supply the medical fluid to the infusion line; an infusion apparatus arranged on the infusion line;
a sensor configured to emit a pressure signal indicative of a pressure of the medical fluid in the infusion line; and a processor configured to receive the pressure signal and to determine a patient signal indicative of a vital signal of the patient based on the pressure signal;

wherein the infusion apparatus includes a pump;

wherein the IV infusion set further comprises:
a compliance element configured to attenuate pressure variations of medical fluid the infusion line; and
a resistance element configured to reflect pressure waves moving along the infusion line;

wherein the sensor is arranged on the infusion line at a position downstream from the resistance element with respect to a direction of fluid flow along the infusion line from the medical fluid source towards the patient access, wherein the compliance element is arranged downstream from the pump with respect to the direction of fluid flow along the infusion line from the medical fluid source towards the patient access, and wherein the compliance element is arranged upstream from the resistance element with respect to the direction of fluid flow along the infusion line from the medical fluid source towards the patient access, wherein the resistance element restricts flow of the medical fluid along the infusion line through the resistance element and the compliance element comprises a drip chamber.

2. The IV infusion set of claim 1, further comprising an additional drip chamber arranged downstream from the medical fluid source with respect to the direction of fluid flow along the infusion line from the medical fluid source towards the patient access; wherein the additional drip chamber is arranged upstream from the pump with respect to the direction of fluid flow along the infusion line from the medical fluid source towards the patient access.

3. The IV infusion set of claim 1, wherein the resistance element comprises a hollow body interposed along the infusion line to allow passage of the medical fluid, the hollow body having a fluid passage section smaller than a fluid passage section of the infusion line defining a section restriction for the medical fluid flow, the hollow body defining a portion of the medical fluid path.

4. The IV infusion set of claim 3, wherein the hollow body includes a slender hollow body and has a longitudinal axis coincident with a longitudinal axis of the infusion line and a passage section smaller than a passage section of the infusion line; the hollow body being made of a material more rigid than the material of the infusion line.

5. The IV infusion set of claim 1, wherein the resistance element is directly connected to an outlet of the compliance element, and comprises a needle.

6. The IV infusion set of claim 1, further comprising a second resistance element, wherein:
the second resistance element is arranged on the infusion line upstream from the compliance element with respect to the direction of fluid flow along the infusion line from the medical fluid source towards the patient access; and
the second resistance element comprises a second hollow body interposed along the infusion line to allow passage of the medical fluid, the second hollow body having a fluid passage section smaller than a fluid passage section of the infusion line defining a section restriction for the medical fluid flow; wherein the second hollow body includes a slender hollow body and defines a portion of the medical fluid path.

7. The IV infusion set of claim 6, wherein the second resistance element includes a needle.

8. The IV infusion set of claim 1, wherein:
the resistance element is arranged downstream from the pump with respect to the direction of fluid flow along the infusion line from the medical fluid source towards the patient access, the patient signal being indicative of at least one of: a peripheral venous pressure, a heart rate of a patient, a respiratory rate of a patient.

9. The IV infusion set of claim 1, further comprising:
a fluid connector placed in correspondence of the first end of the infusion line, the source of medical fluid comprising a container, the fluid connector being configured to fluidly couple the infusion line with the container of medical fluid; wherein the container includes one of a bag and a bottle; and
a flow regulator configured to selectively restrict a fluid flow passage inside the infusion line, said flow regulator being configured to progressively squeeze a portion of the infusion line thereby reducing the fluid flow passage;
wherein the pump is a positive displacement pump configured to operate on the external of a tube portion of the infusion line to convey medical fluid along the direction of fluid flow.

10. The IV infusion set of claim 1, wherein the infusion line includes a pressure coupling configured to be coupled and to cooperate with the sensor to allow the sensor to estimate the pressure signal, wherein the pressure coupling comprises a flat and elastic membrane configured to deform based on a pressure of the fluid flowing inside the infusion line; wherein the pressure coupling comprises a rigid body including an inlet port to receive an inlet tubing portion of the infusion line and an outlet port to receive an outlet tubing portion of the infusion line, the rigid body defining an inner housing divided by the flat and elastic membrane into a first chamber in fluid communication with both the inlet and outlet ports and a second air chamber isolated the first chamber.

11. The IV infusion set of claim 1, wherein the sensor includes a transducer to detect a parameter indicative of a pressure signal along the infusion line and provide an electric signal function of the detected parameter; wherein the sensor further includes a measurement module configured to receive the electric signal from the transducer and to determine the pressure signal based on the electric signal.

12. The IV infusion set of claim 1, wherein the infusion line includes a main infusion line and an auxiliary infusion line connected to the main infusion line and having a first end configured to connect to an auxiliary source of medical fluid and an opposite second end configured to deliver the medical fluid towards the main infusion line, the auxiliary infusion line defining at least a medical fluid path developing from the first end of the auxiliary infusion line to the patient access, the auxiliary source of medical fluid being coupled to the first end of the auxiliary infusion line and configured to supply medical fluid to the auxiliary infusion line, the IV infusion set further comprising:
the auxiliary source of medical fluid;
an auxiliary infusion apparatus arranged on the auxiliary infusion line; and
an auxiliary sensor configured to emit an auxiliary pressure signal indicative of a pressure of a medical fluid in the at least one auxiliary infusion line.

13. The IV infusion set of claim 12, further comprising, for each auxiliary infusion line:
an auxiliary compliance element configured to attenuate pressure variations of medical fluid in the respective auxiliary infusion line; and an auxiliary resistance element configured to reflect pressure waves moving along the auxiliary infusion line; wherein
the compliance element and the resistance element are arranged on the main infusion line and the auxiliary compliance element and the auxiliary resistance element are arranged on the auxiliary infusion line proximate the connection to the main infusion line.

14. The IV infusion set of claim 1, wherein the compliance element has an inlet port and an outlet port for the medical fluid and defines a portion of the medical fluid path.

15. The IV infusion set of claim 1, further comprising a second resistance element directly connected to an inlet of the compliance element, the second resistance element including one of: a 16 G needle, an 18 G needle, a 20 G needle, a 22 G needle, a 24 G needle, and a 27 G needle.

16. The IV infusion set of claim 1, wherein the pump includes one of a peristaltic pump and a finger pump.

17. The IV infusion set of claim 1, wherein the sensor is coupled to an injection port comprising a first section in fluid communication with an internal volume of the infusion line, a second section including an external volume, the sensor being coupled to the external volume and configured to generate a secondary pressure signal based on a pressure in the external volume, and a membrane separating the first section from the second section, the processor being configured to receive the secondary pressure signal and to determine the pressure signal based on the secondary pressure signal.

18. The IV infusion set of claim 1, wherein the infusion line is made of a flexible material and the resistance element comprises a hollow body interposed along the infusion line to allow passage of the medical fluid, the infusion line having a substantially circular fluid passage cross section and the hollow body having a fluid passage cross section smaller than the fluid passage cross section of the infusion line defining a section restriction for the medical fluid flow, the hollow body defining an elongated portion of the medical fluid path.

19. The IV infusion set of claim 1, wherein the resistance element comprises a hollow body interposed along the infusion line with an elongated fluid passage to allow passage of the medical fluid, the hollow body receiving fluid from a portion of the infusion line, conveying the fluid along the elongated fluid passage and delivering fluid to a subsequent portion of the infusion line, at least an inlet of the elongated fluid passage having a fluid passage cross section smaller than a fluid passage cross section of the infusion line.

20. An infusion line for medical fluid, the infusion line comprising:
a first end configured to connect to a source of a medical fluid;
an opposite second end configured to deliver the medical fluid towards a patient access, the infusion line defining a medical fluid path developing from the first end of the infusion line to the patient access;
a compliance element configured to attenuate pressure variations of the medical fluid in the infusion line; and
a resistance element configured to reflect pressure waves moving along the infusion line; wherein based on a direction of fluid flow of the medical fluid through the infusion line from the first end towards the second end, the resistance element is arranged downstream from the compliance element and upstream the second end
wherein the compliance element is arranged downstream from a pump with respect to the direction of fluid flow along the infusion line from the source of the medical fluid towards the patient access, and
wherein the compliance element is arranged upstream from the resistance element with respect to the direction of fluid flow along the infusion line from the source of medical fluid towards the patient access, wherein the resistance element restricts flow of medical fluid along the infusion line through the resistance element and the compliance element comprises a drip chamber.

21. The infusion line of claim 20, wherein:
the resistance element restricts flow of medical fluid along the infusion line through the resistance element; and
the compliance element having an inlet port and an outlet port for the medical fluid and defining a portion of the medical fluid path.

22. The infusion line of claim 20, wherein the infusion line further comprises:
a sensor configured to emit a signal indicative of a pressure of the medical fluid in the infusion line; the sensor being arranged downstream from the resistance element and upstream the second end;
at least one auxiliary infusion line connected to the infusion line; and
an additional drip chamber arranged downstream from the first end with respect to the direction of fluid flow.

23. The infusion line of claim 22, further comprising a pressure coupling configured to be coupled and to cooperate with the sensor to allow the sensor to estimate the pressure signal.

24. The infusion line of claim 20, wherein the resistance element comprises a hollow body interposed along the infusion line to allow passage of the medical fluid, the hollow body defining a portion of the medical fluid path and having a fluid passage section smaller than a fluid passage section of the infusion line defining a section restriction for the medical fluid flow, wherein the hollow body is made of a material more rigid than the material of the infusion line.

25. The infusion line of claim 20, further comprising a fluid connector placed in correspondence of the first end of the infusion line, the fluid connector being configured to connect to the source of the medical fluid comprising a container, the fluid connector being configured to fluidly couple the infusion line with the container of medical fluid.

* * * * *